(12) United States Patent
Biju et al.

(10) Patent No.: US 9,206,196 B1
(45) Date of Patent: Dec. 8, 2015

(54) DERIVATIVES OF BENZOXAZINO QUINOLINE, BENZOXAZINO ISOQUINOLINE AND PROCESSES FOR THEIR PREPARATION

(71) Applicant: Council of Scientific & Industrial Research, New Delhi (IN)

(72) Inventors: Akkattu Thankappan Biju, Maharashtra (IN); Anup Bhunia, Maharashtra (IN); Dhanasekaran Shanmugam, Maharashtra (IN)

(73) Assignee: Council of Scientific & Industrial Research, New Dehli, IN (US)

( * ) Notice: Subject to any disclaimer, the term of this patent is extended or adjusted under 35 U.S.C. 154(b) by 0 days.

(21) Appl. No.: 14/470,839

(22) Filed: Aug. 27, 2014

(30) Foreign Application Priority Data

Jul. 11, 2014 (IN) .......................... 1943/DEL/2014

(51) Int. Cl.
C07D 498/04 (2006.01)
A61K 31/5365 (2006.01)
C07F 17/02 (2006.01)
C07D 498/14 (2006.01)
C07D 498/20 (2006.01)

(52) U.S. Cl.
CPC ............ *C07D 498/04* (2013.01); *C07D 498/14* (2013.01); *C07D 498/20* (2013.01); *C07F 17/02* (2013.01)

(58) Field of Classification Search
CPC .......................... C07D 498/04; A61K 31/5365
USPC ......................................... 544/89; 514/229.5
See application file for complete search history.

(56) References Cited

PUBLICATIONS

Biju et al. Organic Letters (2013), 15(17), 4620-4623.*
Liu et al. Tetrahedron (2013), 69(48), 10405-10413.*

* cited by examiner

*Primary Examiner* — Kahsay Habte
(74) *Attorney, Agent, or Firm* — Knobbe Martens Olson & Bear, LLP

(57) ABSTRACT

Novel benzoxazino quinoline derivatives of Formula (I) and benzoxazino isoquinoline derivatives of Formula (II) are provided:

Formula (I)

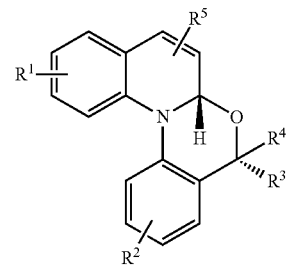

Formula (II)

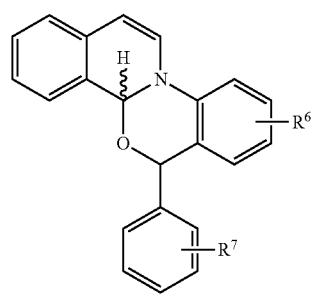

Also provided is a transition-metal-free multicomponent reaction of arynes, N-heterocycles, and carbonyl compounds leading to the diastereoselective synthesis of benzoxazino quinoline derivatives of Formula (I) and benzoxazino isoquinoline derivatives of formula (II) in good yields proceeding via 1,4-zwitterionic intermediates. The compounds possess anti-malarial activity.

14 Claims, 2 Drawing Sheets

DERIVATIVES OF BENZOXAZINO QUINOLINE, BENZOXAZINO ISOQUINOLINE AND PROCESSES FOR THEIR PREPARATION

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of Indian Provisional Application 1943/DEL/2014, filed on Jul. 11, 2014. The aforementioned application is incorporated by reference herein in its entirety, and is hereby expressly made a part of this specification.

FIELD OF THE INVENTION

Novel benzoxazino quinoline derivatives of Formula (I) and benzoxazino isoquinoline derivatives of Formula (II) are provided:

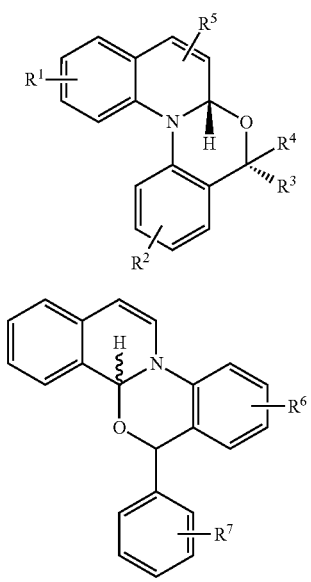

Also provided is a process for the preparation of benzoxazino quinoline derivatives and benzoxazino isoquinoline derivatives involving transition-metal-free multicomponent reaction of arynes, N-Heterocycles, and carbonyl compounds via formation of 1,4-zwitterionic intermediates.

BACKGROUND

Multicomponent Reactions (MCRs) are one-pot reactions, in which three or more starting materials react to form a product, where basically all or most of the atoms contribute to the newly formed product. Speed, diversity, efficiency, atom-economy and environmental friendliness are some of the notable features of this class of reactions. The most important MCRs are the isocyanide-based reactions such as the Passerini three-component reaction and the Ugi four-component reaction. Moreover, a variety of heterocycles can be constructed using the MCR strategy, where zwitterionic intermediates are generated by the addition of nucleophile to activated C—C multiple bonds followed by their interception with a third component.

The synthetic utility of arynes in MCRs has been recently significant as this method allows a straightforward access to various multisubstituted arenes of structural complexity and diversity. The initial reports on aryne MCRs utilize the anionic nucleophiles as the nucleophilic trigger. Arynes are highly electrophilic reactive intermediates, which have been extensively utilized in various carbon-carbon and carbon-heteroatom bond-forming reactions. Arynes have been employed for the construction of multisubstituted arenes of structural diversity and complexity. This kinetically unstable intermediate can react with a wide variety of anionic and uncharged nucleophiles leading to a direct approach to access 1,2-disubstituted arenes, which are structural fragments in many natural compounds as well as biologically active compounds.

Hence the process for the preparation of these compounds and newer forms is an area of continuous research. One of the important aspects of aryne chemistry is multicomponent reaction, which mainly include the initial addition of nucleophiles to arynes and subsequent trapping of the aryl anion intermediate with electrophiles. If the nucleophile and electrophile do not belong to the same molecule, the overall process is a unique three-component coupling, where the aryne is inserted between the other two coupling partners. This versatile transition-metal-free methodology has been applied to the synthesis of valuable heterocycles and in natural product synthesis.

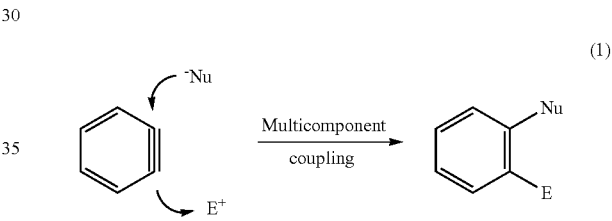

Article titled "Arynes in a Three-Component Coupling Reaction: Straightforward Synthesis of Benzoannulated Iminofurans" by Hiroto Yoshida et al. published in *Angewandte Chemie International Edition*, 2004, 43 (30), pages 3935-3938 reports a variety of benzoannulated iminofurans obtained from an aryne, an isocyanide, and an aldehyde in modest to high yields.

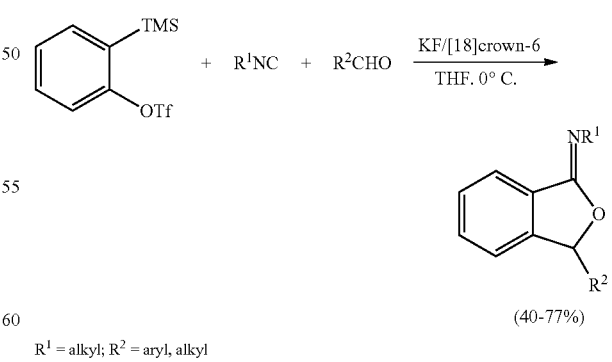

Yoshida, Kunai and coworkers employed isocyanides as the neutral nucleophile source and they reported an efficient MCR involving arynes, isocyanides and aldehydes leading to the formation of benzannulated iminofuran derivatives. Interestingly, however, the synthetic utility of N-heterocycles as nucleophiles in aryne MCRs has got only limited attention.

Article titled "Three-Component Coupling of Arynes, Aminosilanes, and Aldehydes" by Hiroto Yoshida et al. published in *Organic Letters,* 2007, 9 (17), pp 3367-3370 reports a three-component coupling of arynes, aminosilanes, and aldehydes enables diverse amino and hydroxymethyl groups to be incorporated directly into 1,2-positions of aromatic rings. The reaction carried out in presence of KF and 18-Crown-6 in THF solvent.

Article titled "Arynes in Transition-Metal-Free Multicomponent Coupling Reactions" by S Bhojgude et al. published in *Angewandte Chemie International Edition,* 2012, 51 (7), pages 1520-1522 reports the multicomponent reactions involving arynes offer direct access to unusual heterocyclic scaffolds and 1,2-disubstituted arenes. The transition-metal-free multicomponent coupling reactions between arynes, isocyanides and terminal alkynes.

Article titled "Strategies for Heterocyclic Construction via Novel Multicomponent Reactions Based on Isocyanides and Nucleophilic Carbenes" by Vijay Nair et al published in *Acc. Chem. Res.,* 2003, 36 (12), pp 899-907 reports that rea of multicomponent reactions (MCRs) involving zwitterionic species generated by the addition of isocyanides and nucleophilic carbenes such as dimethoxycarbene and N-heterocyclic carbenes to activated alkynes. The strategy employed encompasses the interception of 1:1 zwitterionic species, generated in situ with a wide range of electrophiles.

Article titled "Transition-Metal-Free Multicomponent Reactions Involving Arynes, N-Heterocycles, and Isatins" by Anup Bhunia et al. in *Angewandte Chemie,* 2013, 125 (38), pages 10224-10227 reports transition metal free multicomponent reaction involving arynes, N-heterocycles and N-substituted isatins, when the isoquinoline is used as the nucleophile, the reaction furnishes the spirooxazino isoquinoline analogues of Formula (I) and when pyridine is used as nucleophilic trigger, the reaction affords indolin 2-one analogues, wherein the reaction is carried out under mild condition in presence of KF and [18]-crown-6 in suitable organic solvents.

Multicomponent reaction using aryne is known in the art, but utilizing N-heteroaromatic compounds as the nucleophilic trigger is very rare.

SUMMARY

Novel benzoxazino quinoline and isoquinoline derivatives and economically and industrially feasible process for preparation thereof have been developed, wherein the process is transition-metal free and multicomponent reaction to afford high yield and selectivity of desired products.

The main object is to provide novel benzoxazino quinoline derivatives of Formula (I) and novel benzoxazino isoquinoline derivatives of Formula (II).

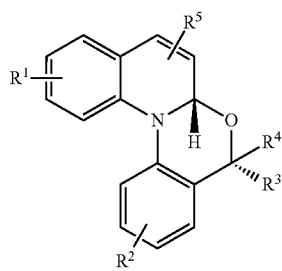

Formula (I)

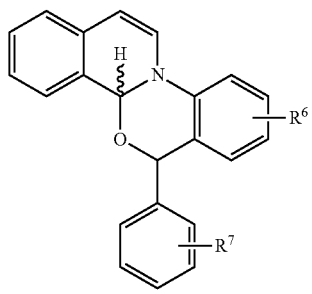

Formula (II)

Another object is to provide process for the synthesis of benzoxazino quinoline derivatives and novel benzoxazino isoquinoline derivatives.

Yet another object is to provide transition-metal-free, multicomponent reaction (MCR) process for the preparation of diastereoselective benzoxazino quinoline derivatives and benzoxazino isoquinoline derivatives.

Accordingly, novel benzoxazino quinoline derivatives of Formula (I) are provided:

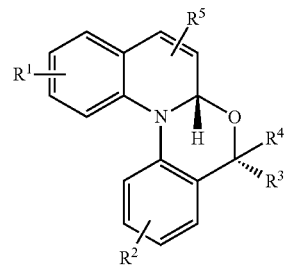

Formula (I)

In an aspect, novel benzoxazino isoquinoline derivatives of Formula (II) are provided:

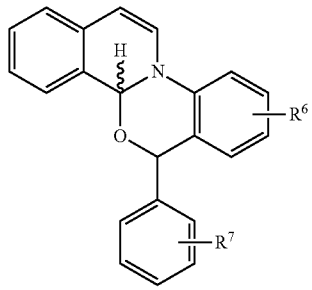

Formula (II)

In another aspect, a transition-metal-free, multicomponent reaction (MCR) process is provided for the preparation of diastereoselective benzoxazino quinoline derivatives Formula (I) comprising quinoline triggered coupling of aryne precursor and carbonyl compound in presence of KF and 18-crown-6 in THF solvent.

In another aspect, a transition-metal-free, multicomponent reaction (MCR) process is provided for the preparation of diastereoselective benzoxazino isoquinoline derivatives Formula (II) in comprising isoquinoline triggered coupling of aryne precursor and carbonyl compound in presence of KF and 18-crown-6 in THF solvent.

DETAILED DESCRIPTION OF THE EMBODIMENTS

Figure 1:
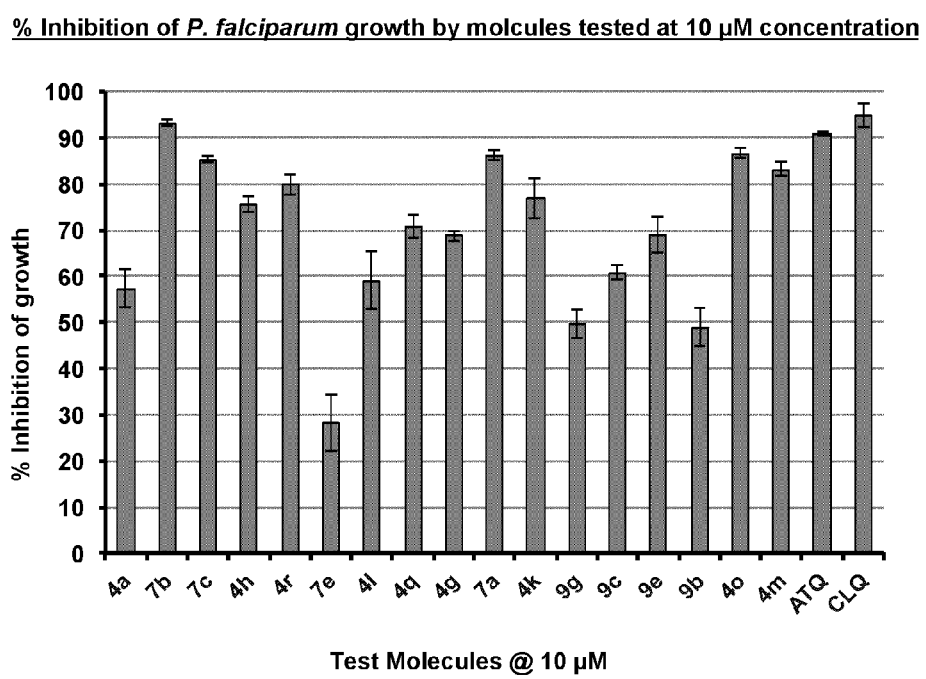
FIG. 1: Data from preliminary screen depicting % inhibition of growth of malaria parasites treated with respective molecules at 10 μM. Standard anti-malarial compounds atovaquone (ATQ) and chloroquine (CLQ) were tested at 1 μM.

The invention will now be described in detail in connection with certain preferred and optional embodiments, so that various aspects thereof may be more fully understood and appreciated.

In an embodiment, novel benzoxazino quinoline derivatives of Formula (I) are provided:

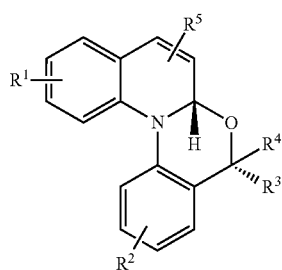

Formula (I)

Wherein,
$R^1$ is H, ($C_1$ to $C_6$) alkoxy, $R^2$ is H, ($C_1$ to $C_6$) alkyl, aryl, fluoro, dioxane ring O—($CH_2$)—O, $R^3$ is H, ($C_1$ to $C_6$) alkyl, aryl, arylalkyl, cycloalkyl, ferrociene, —COR, $R^4$ is H, ($C_1$ to $C_6$) alkyl, aryl, arylalkyl, cyclohexyl, ferrociene, —COR, R is aryl, alkoxy $R^5$ is hydrogen, ($C_1$ to $C_6$) alkyl,
Wherein the aryl rings may be optionally substituted with one or more halogens, Wherein $R^3$ and $R^4$ may optionally form a cyclic ring and process for preparation thereof.

In preferred embodiment, the representative compounds of Formula (I) when the carbonyl compound selected from aldehyde comprising;
(i) 5-(4-Chlorophenyl)-5H,6aH-benzo[4,5][1,3]oxazino[3,2-a]quinoline (4a),
(ii) 5-(4-Methoxyphenyl)-5H,6aH-benzo[4,5][1,3]oxazino[3,2-a]quinoline (4b),
(iii) 5-Phenyl-5H,6aH-benzo[4,5][1,3]oxazino[3,2-a]quinoline (4c),
(iv) 5-(4-Fluorophenyl)-5H,6aH-benzo[4,5][1,3]oxazino[3,2-a]quinoline (4d),
(v) 5-(3-Bromophenyl)-5H,6aH-benzo[4,5][1,3]oxazino[3,2-a]quinoline (4e),
(vi) 5-(2-Fluorophenyl)-5H,6aH-benzo[4,5][1,3]oxazino[3,2-a]quinoline (4d)
(vii) 5-(3,4-Dichlorophenyl)-5H,6aH-benzo[4,5][1,3]oxazino[3,2-a]quinoline (4g)
(viii) 5-(Naphthalen-2-yl)-5H,6aH-benzo[4,5][1,3]oxazino[3,2-a]quinoline (4h)
(ix) 5-(Thiophen-2-yl)-5H,6aH-benzo[4,5][1,3]oxazino[3,2-a]quinoline (4i)
(x) 5-(Thiophen-3-yl)-5H,6aH-benzo[4,5][1,3]oxazino[3,2-a]quinoline (4j)
(xi) 5-Ferrocineyl-5H,6aH-benzo[4,5][1,3]oxazino[3,2-a]quinoline (4k)
(xii) 5-Cyclohexyl-5H,6aH-benzo[4,5][1,3]oxazino[3,2-a]quinoline (4l)
(xiii) 5-(4-Chlorophenyl)-8-methyl-5H,6aH-benzo[4,5][1,3]oxazino[3,2-a]quinoline (4m)
(xiv) 5-(4-Chlorophenyl)-12-methoxy-5H,6aH-benzo[4,5][1,3]oxazino[3,2-a]quinoline (4n)
(xv) 5-(4-Chlorophenyl)-2,3-dimethyl-5H,6aH-benzo[4,5][1,3]oxazino[3,2-a]quinoline (4o)
(xvi) 5-(4-Chlorophenyl)-2,3-difluoro-5H,6aH-benzo[4,5][1,3]oxazino[3,2-a]quinoline (4p)
(xvii) 8-(4-Chlorophenyl)-6aH,8H-[1,3]dioxolo[4",5":4',5']benzo[1',2':4,5][1,3]oxazino[3,2-a]quinoline (4q)
(xviii) 5-Phenyl-5H,6aH-naphtho[2',1':4,5][1,3]oxazino[3,2-a]quinoline (4r)

According to the above embodiment, the benzoxazino quinoline derivatives of Formula (I) encompasses the compounds (4a-4r) listed herein below Table 1.

TABLE 1

| Sr. No. | IUPAC Name | Structure | Yield (%) |
|---|---|---|---|
| 1. | 5-(4-Chlorophenyl)-5H,6aH-benzo[4,5][1,3]oxazino[3,2-a]quinoline (4a) | 4a | 68 |

TABLE 1-continued

| Sr. No. | IUPAC Name | Structure | Yield (%) |
|---|---|---|---|
| 2. | 5-(4-Methoxyphenyl)-5H,6aH-benzo[4,5][1,3]oxazino[3,2-a]quinoline (4b) | 4b | 66 |
| 3. | 5-Phenyl-5H,6aH-benzo[4,5][1,3]oxazino[3,2-a]quinoline (4c) | 4c | 82 |
| 4. | 5-(4-Fluorophenyl)-5H,6aH-benzo[4,5][1,3]oxazino[3,2-a]quinoline (4d) | 4d | 96 |
| 5. | 5-(3-Bromophenyl)-5H,6aH-benzo[4,5][1,3]oxazino[3,2-a]quinoline (4e) | 4e | 65 |
| 6. | 5-(2-Fluorophenyl)-5H,6aH-benzo[4,5][1,3]oxazino[3,2-a]quinoline (4f) | 4f | 58 |

TABLE 1-continued

| Sr. No. | IUPAC Name | Structure | Yield (%) |
|---|---|---|---|
| 7. | 5-(3,4-Dichlorophenyl)-5H,6aH-benzo[4,5][1,3]oxazino[3,2-a]quinoline (4g) | 4g | 67 |
| 8. | 5-(Naphthalen-2-yl)-5H,6aH-benzo[4,5][1,3]oxazino[3,2-a]quinoline (4h) | 4h | 50 |
| 9. | 5-(Thiophen-2-yl)-5H,6aH-benzo[4,5][1,3]oxazino[3,2-a]quinoline (4i) | 4i | 57 |
| 10. | 5-(Thiophen-3-yl)-5H,6aH-benzo[4,5][1,3]oxazino[3,2-a]quinoline (4j) | 4j | 69 |
| 11. | 5-Ferrocineyl-5H,6aH-benzo[4,5][1,3]oxazino[3,2-a]quinoline (4k) | 4k | 47 |

TABLE 1-continued

| Sr. No. | IUPAC Name | Structure | Yield (%) |
|---|---|---|---|
| 12. | 5-Cyclohexyl-5H,6aH-benzo[4,5][1,3]oxazino[3,2-a]quinoline (4l) | 4l | 89 |
| 13. | 5-(4-Chlorophenyl)-8-methyl-5H,6aH-benzo[4,5][1,3]oxazino[3,2-a]quinoline (4m) | 4m | 50 |
| 14. | 5-(4-Chlorophenyl)-12-methoxy-5H,6aH-benzo[4,5][1,3]oxazino-[3,2-a]quinoline (4n) | 4n | 65 |
| 15. | 5-(4-Chlorophenyl)-2,3-dimethyl-5H,6aH-benzo[4,5][1,3]oxazino-[3,2-a]quinoline (4o) | 4o | 65 |
| 16. | 5-(4-Chlorophenyl)-2,3-difluoro-5H,6aH-benzo[4,5][1,3]oxazino[3,2-a]quinoline (4p) | 4p | 68 |

TABLE 1-continued

| Sr. No. | IUPAC Name | Structure | Yield (%) |
|---|---|---|---|
| 17. | 8-(4-Chlorophenyl)-6aH,8H-[1,3]dioxolo[4'',5'':4',5']benzo-[1',2':4,5][1,3]oxazino[3,2-a]quinoline (4q) | 4q | 88 |
| 18. | 5-(4-chloro)-Phenyl-5H,6aH-naphtho[2',1':4,5][1,3]oxazino-[3,2-a]quinoline (4r) | 4r | 67 |

In another preferred embodiment, the representative compounds of Formula (I) comprising;

(i) 5,5-Diphenyl-5H,6aH-benzo[4,5][1,3]oxazino[3,2-a]quinoline (7a)

(ii) 6aH-Spiro[benzo[4,5][1,3]oxazino[3,2-a]quinoline-5,1'-cyclohexane]-2',5'-dien-4'-one (7b)

(iii) Phenyl(5-phenyl-5H,6aH-benzo[4,5][1,3]oxazino[3,2-a]quinolin-5-yl)methanone (7c)

(iv) Thiophen-2-yl(5-(thiophen-2-yl)-5H,6aH-benzo[4,5][1,3]oxazino[3,2-a]quinolin-5-yl)methanone (7d)

(v) 5-Phenyl-5H,6aH-benzo[4,5][1,3]oxazino[3,2-a]quinoline-5-carboxylate (7e)

According to the above embodiment, the benzoxazino quinoline derivatives of Formula (I) encompasses the compounds (7a-7e) listed herein below Table 2.

TABLE 2

| Sr. No | IUPAC Name | Structure | Yield (%) |
|---|---|---|---|
| 1. | 5,5-Diphenyl-5H,6aH-benzo[4,5][1,3]-oxazino[3,2-a]quinoline (7a) | 7a | 54 |
| 2. | 6aH-Spiro[benzo-[4,5][1,3]-oxazino[3,2-a]quinoline-5,1'-cyclohexane]-2',5'-dien-4'-one (7b) | 7b | 59 |
| 3. | Phenyl(5-phenyl-5H,6aH-benzo[4,5][1,3]-oxazino[3,2-a]quinolin-5-yl)-methanone (7c) | 7c | 63 |

TABLE 2-continued

| Sr. No | IUPAC Name | Structure | Yield (%) |
|---|---|---|---|
| 4. | Thiophen-2-yl(5-(thiophen-2-yl)-5H,6aH-benzo[4,5][1,3]oxazino[3,2-a]quinolin-5-yl)methanone (7d) | 7d | 56 |
| 5. | 5-Phenyl-5H,6aH-benzo[4,5][1,3]-oxazino[3,2-a]quinoline-5-carboxylate (7e) | 7e | 77 |

In another embodiment, a transition-metal-free, multicomponent reaction (MCR) process is provided for the preparation of diastereoselective benzoxazino quinoline derivatives of Formula (I) comprising quinoline triggered coupling of aryne precursor and carbonyl compound in presence of fluoride source and crown ether in suitable organic solvent.

Accordingly, a process is provided for the preparation of diastereoselective benzoxazino quinoline derivatives of Formula (I) comprises the mixture of 18-crown-6, KF and carbonyl compound was dissolved in THF under argon atmosphere. The resultant reaction mixture was cooled to −10° C. and kept stirring for 5 min followed by addition of quinoline and the aryne precursor. Then the reaction mixture was gradually warmed to room temperature and kept for stirring for 12 hrs. After completion of reaction the crude reaction mixture was purified by column chromatography on silica gel to obtain the corresponding benzoxazino quinoline derivatives as an inseparable mixture of diastereomers in moderate to good yields.

In another preferred embodiment, a process is provided for the preparation of novel benzoxazino quinoline derivatives of Formula (I) comprising the following steps:
a) Dissolving the mixture of 18-crown-6, KF and carbonyl compound in THF under argon atmosphere followed by stirring for 5 min at −10° C.
b) Adding quinoline and aryne precursor to the reaction mixture of step (a) followed by stirring for 12 hrs at room temperature.
c) Purifying the reaction mixture of step (b) to obtain benzoxazino quinolone derivatives of Formula (I).

The quinolines as used herein may optionally be substituted with alkyl or alkoxy group. More preferably, the substituted quinoline are selected from 8-methoxyquinoline, 4-methylquinoline.

The process for the preparation of the benzoxazino quinoline derivatives of Formula (I) comprises carbonyl compound, wherein the carbonyl compound selected from aldehydes and ketones. More preferably, aldehydes are selected from benzaldehyde, 4-chloro-benzaldehyde, 4-methoxybenzaldehyde, 4-fluorobenzaldehyde, 3-bromobenzaldehyde, 2-fluorobenzaldehyde, 3,4-dichlorobenzaldehyde, 2-naphthaldehyde, 2-Thiophene-carboxaldehyde, 3-Thiophenecarboxaldehyde, ferrocienecarboxaldehyde, cyclohexane-carbaldehyde. More preferably, ketones are selected from benzophenone, benzoquinone, benzyl, 1,2-di(thiophen-2-yl)ethane-1,2-dione, ethyl 2-oxo-2-phenylacetate, 4-methylbenzaldehyde, 4-bromobenzaldehyde, The process for the preparation of the benzoxazino quinoline derivatives of Formula (I) comprises aryne precursor, wherein the aryne precursor is preferably selected from the group of 2-(trimethylsilyl)phenyl trifluoromethane sulfonate, 4,5-dimethyl-2-(trimethylsilyl)phenyl trifluoromethanesulfonate, 4,5-difluoro-2-(trimethylsilyl)phenyl trifluoromethanesulfonate, 6-(trimethylsilyl)benzo[d][1,3]dioxol-5-yl trifluoromethanesulfonate, 2-(trimethylsilyl)naphthalen-1-yl trifluoromethane-sulfonate, 4,5-dimethyl-2-(trimethylsilyl) phenyl trifluoromethanesulfonate.

The process for the preparation of novel benzoxazino quinoline derivatives of Formula (I) as shown is Scheme (I):

Scheme (I)

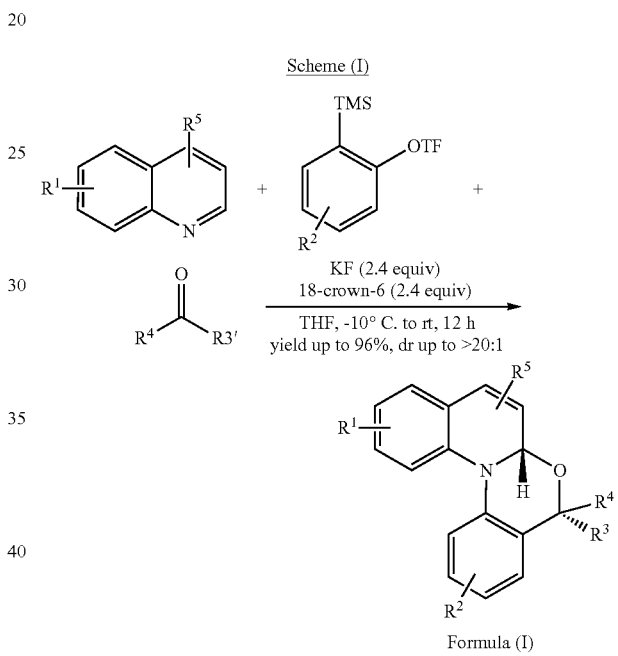

Formula (I)

In an embodiment, novel benzoxazino isoquinoline derivatives of Formula (II) are provided:

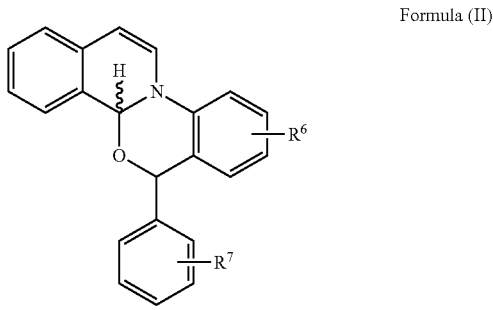

Formula (II)

Wherein $R^6$ is H, $R^7$ is Cl, Br, F and alkyl

In preferred embodiment, representative compound of Formula (II) comprising;
(i) 6-(p-Tolyl)-4bH,6H-benzo[4,5][1,3]oxazino[2,3-a]isoquinoline (9a)

(ii) 6-(4-Bromophenyl)-4bH,6H-benzo[4,5][1,3]oxazino[2,3-a]isoquinoline (9b)
(iii) 6-(4-Chlorophenyl)-4bH,6H-benzo[4,5][1,3]oxazino[2,3-a]isoquinoline (9c)
(iv) 6-(4-Fluorophenyl)-4bH,6H-benzo[4,5][1,3]oxazino[2,3-a]isoquinoline (9d)
(v) 6-(3-Bromophenyl)-4bH,6H-benzo[4,5][1,3]oxazino[2,3-a]isoquinoline (9e)
(vi) 6-(2-Fluorophenyl)-4bH,6H-benzo[4,5][1,3]oxazino[2,3-a]isoquinoline (9f)
(vii) 6-(3,4-Dichlorophenyl)-4bH,6H-benzo[4,5][1,3]oxazino[2,3-a]isoquinoline (9g)
(viii) 8,9-Dimethyl-6-phenyl-4bH,6H-benzo[4,5][1,3]oxazino[2,3-a]isoquinoline (9h)

According to the above embodiment, the benzoxazino isoquinoline derivatives of Formula (II) encompasses the compounds (9a-9h) listed herein below Table 3.

TABLE 3

| Sr. No. | IUPAC Name | Structure | Yield (%) |
|---|---|---|---|
| 1. | 6-(p-Tolyl)-4bH,6H-benzo[4,5][1,3]-oxazino[2,3-a]isoquinoline | 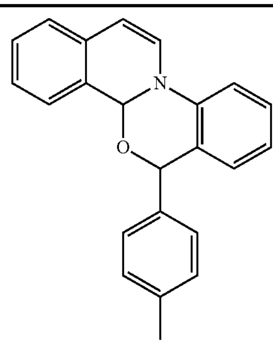 | 80 |
| 2. | 6-(4-Bromophenyl)-4bH,6H-benzo-[4,5][1,3] oxazino [2,3-a]isoquinoline | 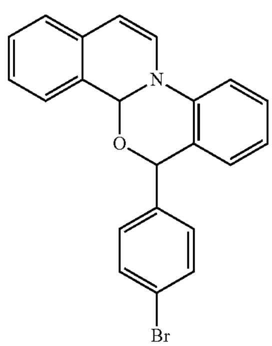 | 82 |
| 3. | 6-(4-Chlorophenyl)-4bH,6H-benzo-[4,5][1,3] oxazino [2,3-a]isoquinoline | 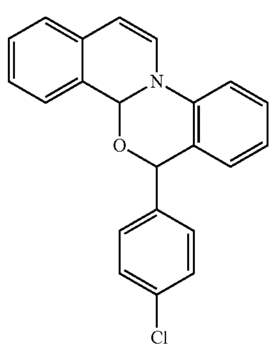 | 81 |

TABLE 3-continued

| Sr. No. | IUPAC Name | Structure | Yield (%) |
|---|---|---|---|
| 4. | 6-(4-Fluorophenyl)-4bH,6H-benzo-[4,5][1,3] oxazino [2,3-a]isoquinoline | 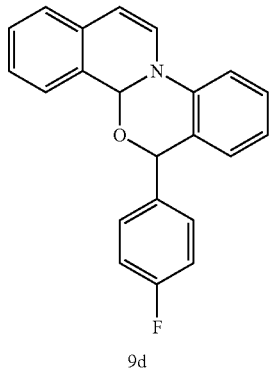 [SMILES: Fc1ccc(C2OC3c4ccccc4C=CN3c3ccccc32)cc1] 9d | 92 |
| 5. | 6-(3-Bromophenyl)-4bH,6H-benzo-[4,5][1,3] oxazino [2,3-a]isoquinoline | 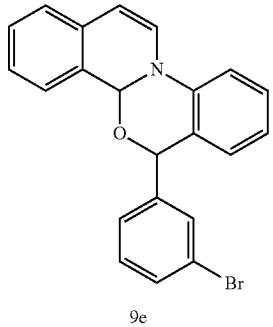 [SMILES: Brc1cccc(C2OC3c4ccccc4C=CN3c3ccccc32)c1] 9e | 62 |
| 6. | 6-(2-Fluorophenyl)-4bH,6H-benzo-[4,5][1,3] oxazino [2,3-a]isoquinoline | 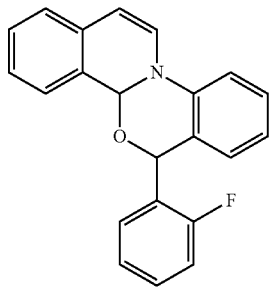 9f | 64 |
| 7. | 6-(3,4-Dichlorophenyl)-4bH,6H-benzo-[4,5][1,3] oxazino [2,3-a]isoquinoline | 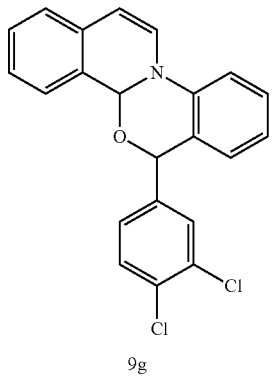 [SMILES: Clc1ccc(C2OC3c4ccccc4C=CN3c3ccccc32)cc1Cl] 9g | 77 |

TABLE 3-continued

| Sr. No. | IUPAC Name | Structure | Yield (%) |
|---|---|---|---|
| 8. | 8,9-Dimethyl-6-phenyl-4bH,6H-benzo-[4,5][1,3] oxazino [2,3-a]iso-quinoline | 9h | 68 |

In another embodiment, a transition-metal-free, multicomponent reaction (MCR) process is provided for the preparation of benzoxazino isoquinoline derivatives of Formula (II) in comprising isoquinoline triggered coupling of aryne precursor and carbonyl compound in presence of fluoride source and crown ether in suitable organic solvent.

Accordingly, a process is provided for the preparation of diastereoselective benzoxazino isoquinoline derivatives of Formula (II) comprises the mixture of 18-crown-6, KF and aldehyde was dissolved in THF under argon atmosphere. The resultant reaction mixture was cooled to −10° C. and kept stirring for 5 min followed by addition of quinoline and the aryne precursor. Then the reaction mixture was gradually warmed to room temperature and kept for stirring for 12 hrs. After completion of reaction the crude reaction mixture was purified by column chromatography on silica gel to obtain the corresponding benzoxazino isoquinoline derivatives as an inseparable mixture of diastereomers in moderate to good yields.

In another preferred embodiment, a process is provided for the preparation of novel benzoxazino isoquinoline derivatives of Formula (II) comprising the following steps:
a) Dissolving the mixture of 18-crown-6, KF and carbonyl compound in THF under argon atmosphere followed by stirring for 5 min at −10° C.
b) Adding isoquinoline and aryne precursor to the reaction mixture of step (a) followed by stirring for 12 hrs at room temperature.
c) Purifying the reaction mixture of step (b) to obtain benzoxazino isoquinolone derivatives of Formula (II).

The process for the preparation of novel benzoxazino isoquinoline derivatives of Formula (II) as shown is scheme (II):

Scheme (II)

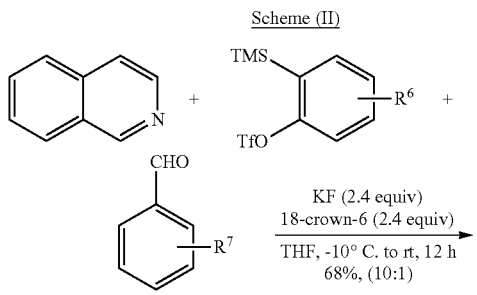

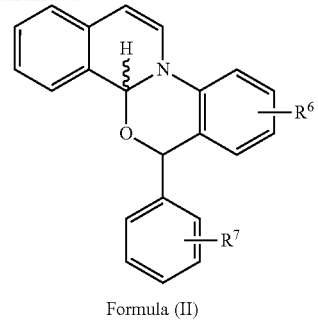

Formula (II)

The process for the preparation of novel benzoxazino isoquinoline derivatives of Formula (II) comprises carbonyl compounds, wherein the carbonyl compound used in above process is selected from aldehydes and ketones. More preferably, aldehydes are selected from 4-chlorobenzaldehyde, 4-fluorobenzaldehyde, 3-bromobenzaldehyde, 2-fluorobenzaldehyde, 3,4-dichlorobenzaldehyde, 4-methylbenzaldehyde, 4-bromobenzaldehyde, The process for the preparation of novel benzoxazino isoquinoline derivatives of Formula (II) comprises aryne precursor, wherein the aryne precursor is preferably selected from the group of 4,5-dimethyl-2-(trimethylsilyl)phenyltrifluoromethanesulfonate, 2-(trimethylsilyl) phenyl trifluoromethanesulfonate.

The optimization studies revealed that the use of other fluoride sources such as tetrabutylammonium fluoride (TBAF) and CsF were not beneficial, and reactions carried out above −10° C. were not efficient.

In another embodiment, a pharmaceutical composition is provided comprising a compound of Formula (I) or Formula (II), or a stereoisomer, or ester or pharmaceutically acceptable salt thereof, and a pharmaceutically acceptable carrier, diluent or excipient.

Further, the compounds of the embodiments are effective as antiplasmodium agent for the treatment of malaria. The compound of Formula (I) or Formula (II) disclosed herein is present in the composition in an amount which is effective to treat the disease or the condition caused by the bacterial strains mentioned above.

The pharmaceutical compositions of the embodiments can be prepared by combining a compound of an embodiment with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres, In another embodiment, a method of administering 'an effective amount' of the 'composition of an embodiment' to the subject suffering from said disease is provided. Accordingly, compound of Formula (I) or (II) and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the embodiments are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

The following examples, which include preferred embodiments, will serve to illustrate the practice of this invention, it being understood that the particulars shown are by way of example and for purpose of illustrative discussion of preferred embodiments of the invention.

EXAMPLES

Unless otherwise specified, all reactions were carried out under an atmosphere of argon in flame-dried reaction vessels with Teflon screw caps. The temperature −10° C. was achieved using the mixture of ice and salt. 25° C. corresponds to the room temperature of the lab when the experiments were carried out. THF was freshly purified by distillation over Na-benzophenone and was transferred under argon. 18-Crown-6 was recrystallized from dry $CH_3CN$ and KF was dried by heating at 110° C. for 12 hrs and left to cool under argon. All aldehydes used in the present study were purchased either from Aldrich, or Acros Organics and were purified either by distillation or washing with $NaHCO_3$ after dissolving in ether, prior to use. The ketone derivatives were purchased from Sigma Aldrich or Acros Organics and were used as received. Benzophenone was purchased from local sources and was purified by flash column chromatography prior to use. Quinoline and isoquinoline were purchased from Aldrich and was purified by distillation prior to use. The 2(trimethylsilyl) phenyl trifluoromethanesulfonate and the other symmetric and unsymmetric aryne precursors were synthesized following literature procedure.

Analytical thin layer chromatography was performed on TLC Silica gel 60 $F_{254}$. Visualization was accomplished with short wave UV light or $KMnO_4$ staining solutions followed by heating. Chromatography was performed on silica gel (230-400 mesh) by standard techniques\eluting with solvents as indicated.

All compounds were fully characterized. $^1H$ and $^{13}C$ NMR spectra were recorded on Bruker AV 400, 500 in solvents as indicated. Chemical shifts (δ) are given in ppm. The residual solvent signals were used as references and the chemical shifts converted to the TMS scale (DMSO-$d_6$: δH=2.51 ppm, δC=39.51 ppm). Infra-red spectra were recorded on a Bruker Alpha-E Infra-red Spectrophotometer. The wave numbers (n) of recorded IR-signals are quoted in $cm^{-1}$. HRMS data were recorded on a Waters SYNAPT G2 High Definition Mass Spectrometry System.

General Procedure for Synthesis of Compounds:

To a flame-dried screw-capped test tube equipped with a magnetic stir bar, added 18-crown-6, KF and carbonyl compound. Then the screw-capped tube was evacuated and backfilled with argon. The mixture was dissolved in THF under argon atmosphere. The resultant reaction mixture was cooled to −10° C. and kept in stirring for 5 min. To the resultant solution was then added quinoline or isoquinoline and the aryne precursor. Then the reaction mixture was kept for stirring at room temperature (25° C.) for 12 hrs. After 12 hrs stirring, the reaction mixture was diluted with EtOAc (2.0 mL) and filtered through short pad of silica gel and eluted with EtOAc (10 mL). The solvent was evaporated to obtain the crude product, which was analyzed using $^1H$ NMR using $CH_2Br_2$ as the internal standard.

Example 1

Synthesis and Characterization of 5-(4-Chlorophenyl)-5H,6aH-benzo[4,5][1,3]oxazino[3,2-a]quinolone (4a)

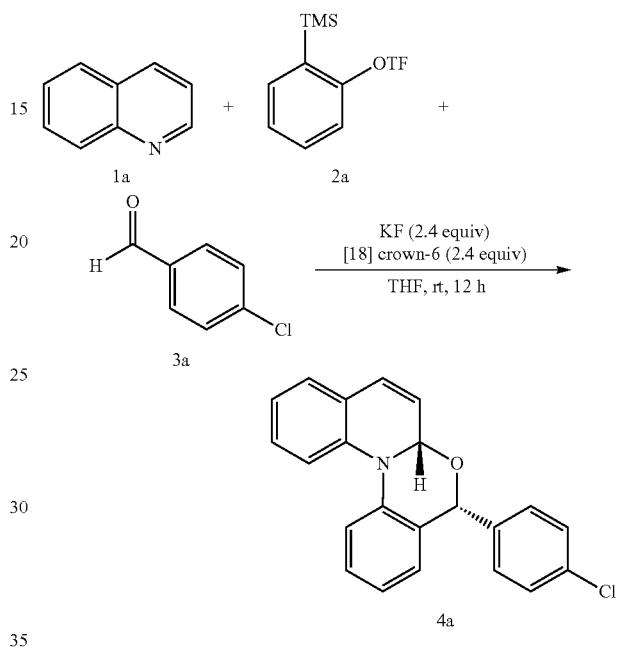

To a flame-dried screw-capped test tube equipped with a magnetic stir bar, added 18-crown-6 (0.159 g, 0.6 mmol), KF (0.035 g, 0.6 mmol) and 4-chlorobenzaldehyde (52.5 mg, 0.375 mmol). Then the screw-capped tube was evacuated and backfilled with argon. The mixture was dissolved in THF (1.0 mL) under argon atmosphere. The resultant reaction mixture was kept in stirring for 5 min. To the resultant solution was then added quinoline (0.25 mmol) and the aryne precursor (0.30 mmol). Then the reaction mixture was kept for stirring at room temperature (25° C.) for 12 hrs. After 12 hrs stirring, the reaction mixture afforded 5-(4-chlorophenyl)-5H,6aH-benzo[4,5][1,3]oxazino[3,2-a]quinoline as inseparable mixture of diastereomers as a white solid (0.118 g, 68% yield, dr determined by $^1H$ NMR analysis of crude reaction mixture is 10:1).

Table 4

| entry | Variation of the standard conditions[a] | Yield of 4a (%)[b] | dr[c] |
|---|---|---|---|
| 1 | None | 43 | 10:1 |
| 2 | TBAF instead of 18-crown-6 and KF | <5 | nd |
| 3[d] | CsF instead of 18-crown-6 and KF | 22 | 10:1 |
| 4 | Reaction at 0° C. to rt | 70 | 6:1 |
| 5 | Reaction at −10° C. tort | 70 (68)[e] | 10:1 |

Optimization Table:

$R_f$ (Pet. ether/EtOAc=60/40): 0.49 $^1H$ NMR (400 MHz, DMSO-$d_6$) δ 7.53 (d, J=7.8 Hz, 1H), 7.40-7.30 (m, 4H), 7.25-7.16 (m, 5H), 7.03 (d, J=7.3 Hz, 1H), 6.92 (d, J=8.2 Hz, 2H), 6.23 (s, 1H), 6.01-5.98 (m, 1H), 5.75 (d, J=4.6 Hz, 1H), $^{13}$C NMR (100 MHz, DMSO-d$_6$) δ 141.25, 139.46, 138.87, 133.48, 132.52, 129.37 (two signals overlapping), 128.55, 128.38, 128.07, 127.99, 126.54, 125.02, 124.75, 120.66, 119.49, 118.43, 112.11, 79.99, 78.77. Representative Peaks of Minor Isomer: $^1$H NMR δ 7.62 (d, J=7.6 Hz), 7.49-7.40 (m), 5.88 (m), 5.68 (m), $^{13}$C NMR δ: 141.68, 135.92, 132.76, 131.31, 130.49, 129.12, 126.76, 124.55, 124.50, 121.38, 118.56, 114.34, 76.16, 75.52 HRMS calculated [M+H]$^+$ for C$_{22}$H$_{17}$ONCl: 346.0993. found: 346.0998. FTIR (cm$_{-1}$) 3393, 3015, 1682, 1654, 1593, 1487, 1456, 1404, 1336, 1285, 1218, 1112, 1068, 1033, 1010, 974, 930, 877, 842, 768, 741, 694, 663, 622.

Example 2

Synthesis and Characterization of 5-(4-Methoxyphenyl)-5H,6aH-benzo[4,5][1,3]oxazino[3,2-a]quinoline (4b)

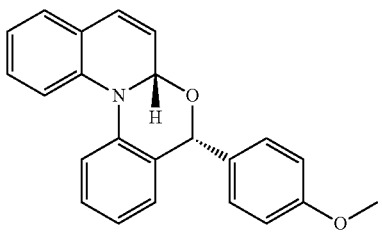

4b

Following the general procedure, treatment of quinoline (0.064g, 59 μL, 0.50 mmol) and 4-methoxybenzaldehyde (0.136 g, 91 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to rt for 12 h followed by flash column chromatography (Pet. ether/EtOAc=75/25) of the crude reaction mixture afforded 5-(4-methoxyphenyl)-5H,6aH-benzo[4,5][1,3]oxazino[3,2-a] quinoline as a yellow solid (0.112 g, 66% yield, dr determined by $^1$H NMR analysis of crude reaction mixture is >20:1).

R$_f$ (Pet. ether/EtOAc=60/40): 0.42 $^1$H NMR (400 MHz, DMSO-d$_6$) δ 7.50 (d, J=7.9 Hz, 1H), 7.34-7.20 (m, 4H), 7.17-7.13 (m, 1H), 7.08 (d, J=8.6 Hz, 2H), 6.98 (d, J=7.7 Hz, 1H), 6.92-6.88 (m, 2H), 6.79 (d, J=8.7 Hz, 2H), 6.14 (s, 1H), 5.99-5.96 (m, 1H), 5.71 (d, J=5.1 Hz, 1H), 3.67 (s, 3H, CH$_3$). $^{13}$C NMR (100 MHz, DMSO-d$_6$) δ 158.93, 139.72, 138.92, 134.37, 134.30, 129.31, 128.93, 128.43, 128.14, 128.02, 126.29, 124.91, 124.70, 120.77, 119.40, 118.65, 113.70, 112.16, 79.96, 79.24, 55.00. HRMS calculated [M+H]$^+$ for C$_{23}$H$_{20}$O$_2$N: 342.1489. found: 342.1497. FTIR (cm$_{-1}$) 3390, 3058, 1933, 1733, 1653, 1620, 1595, 1573, 1499, 1428, 1370, 1314, 1257, 1218, 1119, 1090, 1034, 942, 804, 773, 740, 663.

Example 3

Synthesis and Characterization of 5-Phenyl-5H,6aH-benzo[4,5][1,3]oxazino[3,2-a]quinoline (4c)

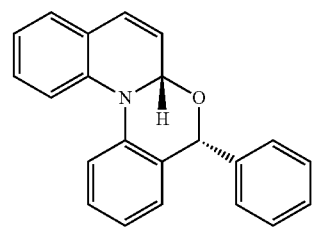

4c

Following the general procedure, treatment of quinoline (0.064 g, 59 μL, 0.50 mmol) and benzaldehyde (0.080 g, 80 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-phenyl-5H,6aH-benzo[4,5][1,3]oxazino[3,2-a]quinoline as a yellow solid (0.128 g, 82% yield, dr determined by $^1$H NMR analysis of crude reaction mixture is >20:1).

R$_f$ (Pet. ether/EtOAc=60/40): 0.53 $^1$H NMR (500 MHz, DMSO-d$_6$) δ 7.52 (d, J=8.0 Hz, 1H), 7.35-7.29 (m, 2H), 7.26-7.23 (m, 5H), 7.17-7.15 (m, 3H), 7.01 (d, J=7.6 Hz, 1H), 6.91 (d, J=9.0 Hz, 2H), 6.20 (s, 1H), 6.01-5.98 (m, 1H), 5.74 (d, J=5.0 Hz, 1H), $^{13}$C NMR (125 MHz, DMSO-d$_6$) δ 142.33, 139.65, 138.91, 134.03, 129.38, 128.53, 128.37, 128.11, 128.08, 127.95, 127.69, 126.42, 125.00, 124.77, 120.74, 119.47, 118.60, 112.19, 79.94, 79.63. HRMS calculated [M+H]$^+$ for C$_{22}$H$_{18}$ON: 312.1383. found: 312.1393. FTIR (cm$^{-1}$) 3744, 3014, 1651, 1594, 1492, 1452, 1420, 1287, 1216, 1120, 1011, 956, 767, 740, 665.

Example 4

Synthesis and Characterization of 5-(4-Fluorophenyl)-5H,6aH-benzo[4,5][1,3]oxazino[3,2-a]quinoline (4d)

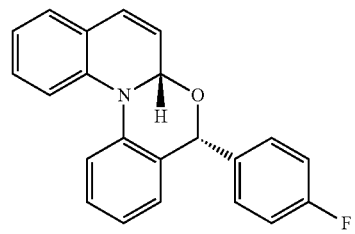

4d

Following the general procedure, treatment of quinoline (0.064 g, 59 μL, 0.50 mmol) and 4-fluorobenzaldehyde (0.093 g, 80 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at 10° C. to room temperature for 12 hrs followed by flash column chromatography (Pet. ether/EtOAc=75/25) of the crude reaction mixture afforded 5-(4-fluorophenyl)-5H,6aH-benzo[4,5][1,3]oxazino[3,2-a]quinoline as inseparable mixture of diastereomers as a yellow solid (0.158 g, 96% yield, dr determined by $^1$H NMR analysis of crude reaction mixture is >20:1).

$R_f$ (Pet. ether/EtOAc=60/40): 0.67 $^1$H NMR (400 MHz, DMSO-$d_6$) δ 7.52 (d, J=7.8 Hz, 1H), 7.36-7.15 (m, 7H), 7.09-7.00 (m, 3H), 6.92-6.89 (m, 2H), 6.23 (s, 1H), 6.00-5.97 (m, 1H), 5.74 (d, J=4.9 Hz, 1H), $^{13}$C NMR (100 MHz, DMSO-$d_6$) δ 161.70 (d, J=244.2 Hz), 139.58, 138.90, 138.58 (d, J=3.4 Hz), 133.83, 129.63 (d, J=8.3 Hz), 129.39, 128.55, 128.08 (two signals are overlapping), 126.52, 124.93 (d, J=23.6 Hz), 120.73, 119.51, 118.52, 115.21 (d, J=21.3 Hz), 112.16, 79.99, 78.82. HRMS calculated [M+H]$^+$ for $C_{22}H_{17}ONF$: 330.1289. found: 330.1296. FTIR (cm$^{-1}$) 3016, 1650, 1600, 1494, 1452, 1418, 1289, 1215, 1157, 1120, 1012, 930, 838, 741, 666.

390.0495. FTIR (cm$^{-1}$) 3746, 3017, 1634, 1593, 1491, 1453, 1288, 1215, 1019, 931, 766, 740, 667.

Example 6

Synthesis and Characterization of 5-(2-Fluorophenyl)-5H,6aH-benzo[4,5][1,3]oxazino[3,2-a]quinoline (4f)

Example 5

Synthesis and Characterization of 5-(3-Bromophenyl)-5H,6aH-benzo[4,5][1,3]oxazino[3,2-a]quinoline (4e)

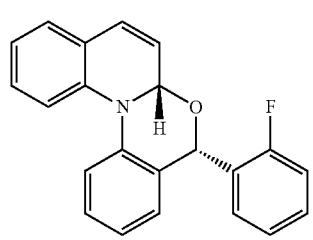

4f

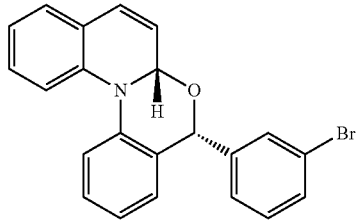

4e

Following the general procedure, treatment of quinoline (0.064 g, 59 μL, 0.50 mmol) and 3-bromobenzaldehyde (0.139 g, 88 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-(3-bromophenyl)-5H,6aH-benzo[4,5][1,3]oxazino[3,2-a]quinoline as a yellow solid (0.127 g, 65% yield, dr determined by $^1$H NMR analysis of crude reaction mixture is >20:1).

$R_f$ (Pet. ether/EtOAc=60/40): 0.47 $^1$H NMR (400 MHz, DMSO-$d_6$) δ 7.52 (d, J=8.0 Hz, 1H), 7.43-7.40 (m, 1H), 7.37-7.30 (m, 3H), 7.24-7.17 (m, 5H), 7.08 (d, J=7.7 Hz, 1H), 6.94-6.90 (m, 2H), 6.21 (s, 1H), 6.02-5.98 (m, 1H), 5.72 (d, J=5.0 Hz, 1H), $^{13}$C NMR (100 MHz, DMSO-$d_6$) δ 145.16, 139.49, 138.87, 133.40, 130.74, 130.59, 130.16, 129.37, 128.63, 128.11, 128.01, 126.67, 126.52, 125.18, 124.87, 121.48, 120.66, 119.57, 118.43, 112.12, 79.88, 78.53, HRMS calculated [M+H]$^+$ for $C_{22}H_{17}ONBr$: 390.0488. found:

Following the general procedure, treatment of quinoline (0.064 g, 59 μL, 0.50 mmol) and 2-fluorobenzaldehyde (0.095 g, 79 μL, 0.75 mmol) with 2-(trimethylsilyl)phenyl trifluoromethane sulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-(2-fluorophenyl)-5H,6aH-benzo[4,5][1,3]oxazino[3,2-a]quinoline as inseparable mixture of diastereomers as a white solid (0.118 g, 58% yield, dr determined by $^1$H NMR analysis of crude reaction mixture is >20:1).

$R_f$ (Pet. ether/EtOAc=60/40): 0.44 $^1$H NMR (500 MHz, DMSO-$d_6$) δ 7.54 (d, J=8.1 Hz, 1H), 7.36 (t, J=7.5 Hz, 1H), 7.31-7.26 (m, 3H), 7.24-7.15 (m, 3H), 7.11 (t, J=9.6 Hz, 1H), 7.06 (t, J=7.4 Hz, 1H), 7.01 (d, J=7.7 Hz, 1H), 6.93-6.89 (m, 2H), 6.48 (s, 1H), 6.01-5.98 (m, 1H), 5.80 (d, J=4.7 Hz, 1H), $^{13}$C NMR (125 MHz, DMSO-$d_6$) δ 160.28 (d, J=248.1 Hz), 139.42 (d, J=23.4 Hz), 133.09, 130.15 (d, J=8.3 Hz), 129.69 (d, J=3.7 Hz), 129.30, 129.04, 128.94, 128.66, 128.02, 127.39, 126.57, 125.09, 124.74, 124.44 (d, J=3.7 Hz), 120.65, 119.44, 118.32, 115.71 (d, J=21.2 Hz), 112.28, 80.16, 73.91, HRMS calculated [M+H]$^+$ for $C_{22}H_{17}ONF$: 330.1289.

found: 330.1297. FTIR (cm$^{-1}$) 3747, 3015, 1651, 1592, 1491, 1453, 1419, 1288, 1216, 1104, 1045, 1013, 929, 878, 768, 741, 666.

Example 7

Synthesis and Characterization of 5-(3,4-Dichlorophenyl)-5H,6aH-benzo[4,5][1,3]oxazino[3,2-a]quinoline (4g)

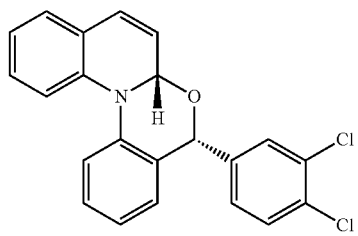

4g

Following the general procedure, treatment of quinoline (0.064 g, 59 μL, 0.50 mmol) and 3,4-dichlorobenzaldehyde (0.130 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-(3,4-dichlorophenyl)-5H,6aH-benzo[4,5][1,3]oxazino[3,2-a]quinoline as a yellow solid (0.127 g, 67% yield, dr determined by $^1$H NMR analysis of crude reaction mixture is >20:1).

$R_f$ (Pet. ether/EtOAc=60/40): 0.58 $^1$H NMR (400 MHz, DMSO-d$_6$) δ 7.53-7.46 (m, 2H), 7.43-7.40 (m, 1H), 7.36-7.29 (m, 2H), 7.21 (d, J=3.8 Hz, 2H), 7.20-7.09 (m, 3H), 6.93-6.89 (m, 2H), 6.24 (s, 1H), 6.01-5.97 (m, 1H), 5.71 (d, J=5.0 Hz, 1H), $^{13}$C NMR (100 MHz, DMSO-d$_6$) δ 143.54, 139.39, 138.86, 133.04, 130.95, 130.70, 130.50, 129.39, 129.36, 128.68, 128.14, 127.97, 127.52, 126.80, 125.24, 124.91, 120.64, 119.63, 118.35, 112.11, 79.92, 77.88. HRMS calculated [M+H]$^+$ for C$_{22}$H$_{16}$ONCl$_2$: 380.0603. found: 380.0609. FTIR (cm$_{-1}$) 3747, 3016, 1652, 1593, 1491, 1456, 1394, 1292, 1214, 1125, 1034, 998, 915, 825, 741, 667, 633.

Example 8

Synthesis and Characterization of 5-(Naphthalen-2-yl)-5H,6aH-benzo[4,5][1,3]oxazino[3,2-a]quinoline (4h)

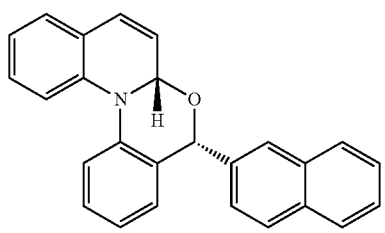

4h

Following the general procedure, treatment of quinoline (0.064 g, 59 μL, 0.50 mmol) and 2-naphthaldehyde (0.117 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-(naphthalen-2-yl)-5H,6aH-benzo[4,5][1,3]oxazino[3,2-a]quinoline as a yellow solid (0.091 g, 50% yield, dr determined by $^1$H NMR analysis of crude reaction mixture is >20:1).

$R_f$ (Pet. ether/EtOAc=60/40): 0.73 $^1$H NMR (400 MHz, DMSO-d$_6$) δ 7.89 (s, 1H), 7.83-7.79 (m, 2H), 7.70 (d, J=8.6 Hz, 1H), 7.55 (d, J=7.9 Hz, 1H), 7.51-7.45 (m, 2H), 7.36-7.24 (m, 4H), 7.14 (t, J=7.6 Hz, 1H), 7.07 (t, J=8.2 Hz, 2H), 6.95-6.91 (m, 2H), 6.36 (s, 1H), 6.04-6.00 (m, 1H), 5.80 (d, J=5.1 Hz, 1H), $^{13}$C NMR (100 MHz, DMSO-d$_6$) δ 139.68, 139.65, 138.99, 133.85, 132.60, 132.57, 129.41, 128.59, 128.19, 128.14, 127.71, 127.52, 126.93, 126.53, 126.33, 126.20, 125.05, 125.03, 124.79, 120.78, 119.54, 118.62, 112.25, 80.00, 79.81. HRMS calculated [M+H]$^+$ for C$_{26}$H$_{20}$ON: 362.1539. found: 362.1548. FTIR (cm$^{-1}$) 3747, 3015, 1651, 1595, 1492, 1452, 1419, 1288, 1215, 1120, 1014, 935, 899, 855, 740, 665.

Example 9

Synthesis and Characterization of 5-(Thiophen-2-yl)-5H,6aH-benzo[4,5][1,3]oxazino[3,2-a]quinoline (4i)

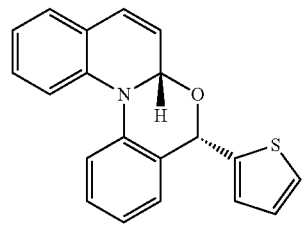

4i

Following the general procedure, treatment of quinoline (0.064 g, 59 μL, 0.50 mmol) and 2-Thiophenecarboxaldehyde (0.084 g, 70 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-(thiophen-2-yl)-5H,6aH-benzo[4,5][1,3]oxazino[3,2-a]quinoline as inseparable mixture of diastereomers as a yellow solid (0.091 g, 57% yield, dr determined by NMR analysis of crude reaction mixture is 1:1).

$R_f$ (Pet. ether/EtOAc=60/40): 0.56 $^1$H NMR (400 MHz, DMSO-d$_6$) δ 7.60-7.56 (m, 1H), 7.50 (d, J=7.7 Hz, 1H), 7.42 (t, J=7.6 Hz, 1H), 7.33 (d, J=5.0 Hz, 1H), 7.29-7.25 (m, 1H), 7.25-7.16 (m, 3H), 7.12 (d, J=3.3 Hz, 1H), 6.93-6.87 (m, 3H), 6.51 (s, 1H), 6.00-5.96 (m, 1H), 5.72 (d, J=5.1 Hz, 1H), $^{13}$C NMR (100 MHz, DMSO-d$_6$) δ 145.80, 139.35, 138.69, 133.53, 129.21, 128.61, 128.12, 127.98, 127.12, 126.78, 126.28, 126.25, 124.94, 124.65, 120.62, 119.44, 118.30, 112.27, 80.05, 74.78. Representative Peaks of Minor Isomer: $^1$H NMR δ 7.37 (d, J=7.0 Hz), 7.10 (d, J=3.1 Hz), 7.06-7.04 (m), 6.20 (s), 5.90-5.86 (m), 5.65 (d, J=4.8 Hz), $^{13}$C NMR δ:

146.63, 138.83, 138.62, 131.21, 129.15, 128.85, 128.82, 128.09, 126.68, 126.73, 126.12, 124.45, 124.34, 120.57, 119.70, 118.34, 112.20, 76.10, 71.65. HRMS calculated [M+H]$^+$ for $C_{20}H_{16}ONS$: 318.0947. found: 318.0958. FTIR (cm$^{-1}$) 3017, 1668, 1634, 1604, 1572, 1489, 1458, 1426, 1365, 1303, 1244, 1214, 1012, 929, 852, 741, 664.

Example 10

Synthesis and Characterization of 5-(Thiophen-3-yl)-5H,6aH-benzo[4,5][1,3]oxazino[3,2-a]quinoline (4j)

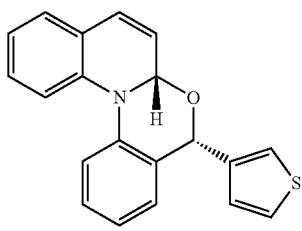

4j

Following the general procedure, treatment of quinoline (0.064 g, 59 μL, 0.50 mmol) and 3-Thiophenecarboxaldehyde (0.084 g, 66 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-(thiophen-3-yl)-5H,6aH-benzo[4,5][1,3]oxazino[3,2-a]quinoline as inseparable mixture of diastereomers as a yellow solid (0.109 g, 69% yield, dr determined by $^1$H NMR analysis of crude reaction mixture is 1:1).

$R_f$ (Pet. ether/EtOAc=60/40): 0.55 $^1$H NMR (500 MHz, DMSO-d$_6$) δ 7.59-7.56 (m, 2H), 7.45 (bs, 1H), 7.34-7.33 (m, 1H), 7.28 (d, J=7.2 Hz, 1H), 7.24-7.16 (m, 4H), 7.05 (d, J=8.2 Hz, 1H), 6.91-6.87 (m, 2H), 5.96 (s, 1H), 5.92-5.88 (m, 1H), 5.67 (d, J=5.0 Hz, 1H), $^{13}$C NMR (125 MHz, DMSO-d$_6$) δ 144.23, 139.00, 138.87, 131.89, 129.12, 128.50, 128.04, 127.53, 126.88, 126.56, 124.50, 124.39, 123.56, 120.56, 119.52, 118.71, 112.16, 76.13, 72.01. Representative Peaks of Minor Isomer: $^1$H NMR δ 7.50 (d, J=7.9 Hz), 7.41 (d, J 7.5 Hz), 7.37 (d, J=5.0 Hz), 7.09 (d, J=8.0 Hz), 6.61 (d, J=4.8 Hz), 6.29 (s), 6.00-5.97 (m), 5.70 (d, J=4.9 Hz), $^{13}$C NMR δ: 143.08, 139.60, 138.80, 133.53, 129.30, 128.54, 127.97, 126.66, 126.48, 126.23, 124.99, 124.77, 124.46, 120.72, 119.43, 118.58, 79.83, 74.90. HRMS calculated [M+H]$^+$ for $C_{20}H_{16}ONS$: 318.0947. found: 318.0955. FTIR (cm$^{-1}$) 3735, 3017, 1653, 1593, 1491, 1451, 1419, 1285, 1215, 1000, 922, 740, 666.

Example 11

Synthesis and Characterization of 5-Ferrocineyl-5H,6aH-benzo[4,5][1,3]oxazino[3,2-a]quinoline (4k)

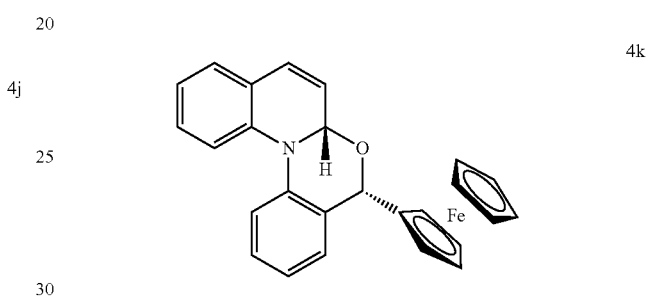

4k

Following the general procedure, treatment of quinoline (0.064 g, 59 μL, 0.50 mmol) and ferrocienecarboxaldehyde (0.161 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=70/30) of the crude reaction mixture afforded 5-ferrocineyl-5H,6aH-benzo[4,5][1,3]oxazino[3,2-a]quinoline as inseparable mixture of diastereomers as a red solid (0.099 g, 47% yield, dr determined by $^1$H NMR analysis of crude reaction mixture is 10:1).

$R_f$ (Pet. ether/EtOAc=60/40): 0.71 $^1$H NMR (400 MHz, DMSO-d$_6$) δ 7.45 (d, J=7.4 Hz, 1H), 7.38 (d, J=7.2 Hz, 1H), 7.33-7.28 (m, 2H), 7.23-7.21 (m, 1H), 7.14 (s, 2H), 6.93 (d, 0.1=9.4 Hz, 1H), 6.87-6.86 (m, 1H), 6.06 (bs, 1H), 5.94 (s, 1H), 5.62 (s, 1H), 4.24 (s, 2H), 4.11 (s, 5H), 3.98 (s, 1H), 3.78 (s, 1H), $^{13}$C NMR (100 MHz, DMSO-d$_6$) δ 139.34, 138.62, 134.35, 129.10, 128.28, 127.97, 127.77, 126.25, 124.62, 124.31, 120.47, 119.16, 118.82, 111.99, 90.96, 79.67, 75.05, 68.63, 67.49, 67.34, 66.92, 65.64. Representative Peaks of Minor Isomer: $^1$H NMR δ 5.65 (s), 5.55 (s), 4.36 (s), 4.29 (s), 4.04 (s), $^{13}$C NMR δ: 139.03, 138.15, 132.82, 129.04, 128.47, 128.20, 124.20, 120.65, 119.44, 112.13, 91.25, 76.79, 72.90, 68.74, 68.20, 65.92. HRMS calculated [M+H]$^+$ for $C_{26}H_{22}FeON$: 420.1045. found: 420.1051. FTIR (cm$^{-1}$)

3418, 2992, 2253, 1647, 1594, 1490, 1451, 1416, 1288, 1215, 1106, 1002, 925, 819, 744, 662.

Example 12

Synthesis and Characterization of 5-Cyclohexyl-5H, 6aH-benzo[4,5][1,3]oxazino[3,2-a]quinoline (4l)

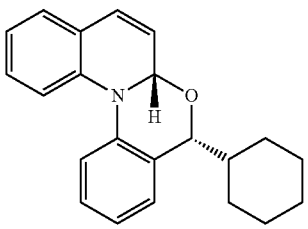

4l

Following the general procedure, treatment of quinoline (0.064 g, 59 μL, 0.50 mmol) and cyclohexanecarbaldehyde (0.084 g, 91 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-cyclohexyl-5H,6aH-benzo[4,5][1,3]oxazino[3,2-a]quinoline as a yellow solid (0.141 g, 89% yield, dr determined by $^1$H NMR analysis of crude reaction mixture is >20:1).

$R_f$ (Pet. ether/EtOAc=60/40): 0.63 $^1$H NMR (500 MHz, DMSO-d$_6$) δ 7.44 (d, J=8.0 Hz, 1H), 7.33-7.28 (m, 2H), 7.24 (d, J=7.4 Hz, 2H), 7.13 (bs, 2H), 6.86-6.82 (m, 2H), 5.97-5.94 (m, 1H), 5.43 (d, J=4.6 Hz, 1H), 5.03 (s, 1H), 1.70-1.63 (m, 3H), 1.48 (d, J=10.7 Hz, 1H), 1.40 (d, J=10.6 Hz, 1H), 1.24-1.15 (m, 2H), 1.00 (d, J=13.1 Hz, 1H), 0.95-0.88 (m, 2H), 0.76-0.69 (m, 1H). $^{13}$C NMR (125 MHz, DMSO-d$_6$) δ 140.00, 139.40, 133.59, 129.08, 128.25, 127.91, 126.67, 125.98, 124.84, 124.02, 120.30, 118.96, 118.88, 111.95, 80.36, 79.13, 44.36, 29.30, 26.11, 25.82, 25.64, 24.54. HRMS calculated [M+H]$^+$ for C$_{22}$H$_{24}$ON: 318.1852. found: 318.1859. FTIR (cm$^{-1}$) 3748, 3014, 2929, 2855, 1651, 1593, 1492, 1451, 1420, 1294, 1216, 1041, 990, 768, 741, 667.

Example 13

Synthesis and Characterization of 5-(4-Chlorophenyl)-8-methyl-5H,6aH-benzo[4,5][1,3]oxazino[3,2-a]quinoline (4m)

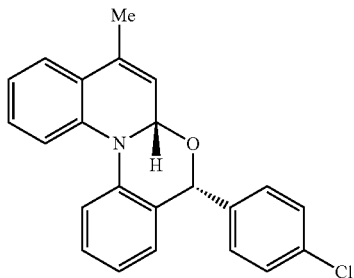

4m

Following the general procedure, treatment of 4-methylquinoline (0.073 g, 66 μL, 0.50 mmol) and 4-chlorobenzaldehyde (0.105 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=50/50) of the crude reaction mixture afforded 5-(4-chlorophenyl)-8-methyl-5H,6aH-benzo[4,5][1,3]oxazino[3,2-a]quinoline as inseparable mixture of diastereomers as a white solid (0.090 g, 50% yield, dr determined by $^1$H NMR analysis of crude reaction mixture is 3:1).

$R_f$ (Pet. ether/EtOAc=60/40): 0.20 $^1$H NMR (500 MHz, DMSO-d$_6$) δ 7.49 (d, J=8.2 Hz, 1H), 7.42 (d, J=7.5 Hz, 2H), 7.36-7.30 (m, 2H), 7.27-7.23 (m, 2H), 7.18 (d, J=8.2 Hz, 3H), 7.02 (d, J=7.8 Hz, 1H), 6.99-6.95 (m, 1H), 6.20 (s, 1H), 5.86 (m, 1H), 5.66 (d, J=5.0 Hz, 1H), 2.18 (s, 3H, CH$_3$)$^{13}$C NMR (125 MHz, DMSO-d$_6$) δ 141.33, 139.69, 139.13, 138.41, 133.72, 133.52, 132.51, 129.41, 129.19, 128.41, 128.04, 126.57, 125.10, 124.77, 121.86, 119.42, 116.48, 112.40, 79.98, 78.51, 18.32. Representative Peaks of Minor Isomer: $^1$H NMR δ 7.69-7.68 (m), 7.76-7.75 (m), 5.58-5.57 (m), 2.16 (s). $^{13}$C NMR δ: 141.80, 133.68, 132.01, 130.50, 129.15, 128.52, 116.54, 76.07, 73.54. HRMS calculated [M+H]$^+$ for C$_{23}$H$_{19}$ONCl: 360.1150. found: 360.1158. FTIR (cm$^{-1}$)

3746, 3013, 1650, 1592, 1484, 1398, 1303, 1265, 1217, 1169, 1086, 985, 937, 812, 766, 740, 666.

Example 14

Synthesis and Characterization of 5-(4-Chlorophenyl)-12-methoxy-5H,6aH-benzo[4,5][1,3]oxazino[3,2-a]quinoline (4n)

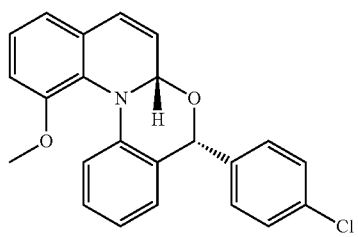

4n

Following the general procedure, treatment of 8-methoxyquinoline (0.086 g, 0.50 mmol) and 4-chlorobenzaldehyde (0.105 g, 0.75 mmol) with 2-(trimethylsilyl)phenyl trifluoromethanesulfonate (0.179 g, 146 µL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=70/30) of the crude reaction mixture afforded 5-(4-chlorophenyl)-5H,6aH-benzo[4,5][1,3]oxazino[3,2-a]quinoline as inseparable mixture of diastereomers as a white solid (0.121 g, 65% yield, dr determined by $^1$H NMR analysis of crude reaction mixture is 1:1).

$R_f$ (Pet. ether/EtOAc=60/40): 0.30 $^1$H NMR (500 MHz, DMSO-$d_6$) δ 7.56-7.51 (m, 2H), 7.44 (s, 1H), 7.28 (d, J=8.2 Hz, 1H), 7.16 (t, J=7.8 Hz, 1H), 7.05-7.01 (m, 2H), 6.97-6.93 (m, 2H), 6.90-6.85 (m, 1H), 6.65-6.61 (m, 1H), 6.24-6.21 (m, 2H), 5.75 (s, 1H), 5.61 (d, J=4.6 Hz, 1H), 3.69 (s, 3H, $CH_3$). $^{13}$C NMR (125 MHz, DMSO-$d_6$) δ 151.72, 149.99, 138.30, 132.87, 131.50, 129.77, 129.46, 129.69, 128.46, 127.95, 127.78, 127.53, 127.01, 124.65, 123.54, 122.38, 119.76, 119.57, 115.34, 114.39, 83.95, 82.08, 55.49. Representative Peaks of Other Isomer: $^1$H NMR δ 7.22 (d, J=8.2 Hz), 5.98-5.92 (m), 3.49 (s), $^{13}$C NMR δ: 147.24, 142.31, 136.88, 132.20, 130.70, 129.56, 128.41, 128.30, 128.27, 128.15, 127.44, 126.67, 125.74, 124.55, 120.95, 118.52, 118.13, 114.21, 112.07, 79.54, 75.57, HRMS calculated [M+H]$^+$ for $C_{23}H_{19}O_2NCl$: 376.1099. found: 376.1103. FTIR (cm$^{-1}$) 3017, 1656, 1596, 1490, 1450, 1411, 1351, 1279, 1215, 1124, 1049, 921, 884, 742, 664.

Example 15

Synthesis and Characterization of 5-(4-Chlorophenyl)-2,3-dimethyl-5H,6aH-benzo[4,5][1,3]oxazino[3,2-a]quinoline (4o)

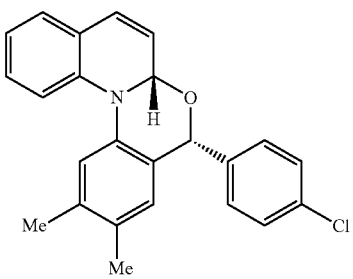

4o

Following the general procedure, treatment of quinoline (0.064 g, 59 µL, 0.50 mmol) and 4-chlorobenzaldehyde (0.105 g, 0.75 mmol) with 4,5-dimethyl-2-(trimethylsilyl)phenyl trifluoromethanesulfonate (0.196 g, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=70/20) of the crude reaction mixture afforded 5-(4-chlorophenyl)-2,3-dimethyl-5H,6aH-benzo[4,5][1,3]oxazino[3,2-a]quinoline as inseparable mixture of diastereomers as a white solid (0.121 g, 65% yield, dr determined by $^1$H NMR analysis of crude reaction mixture is 10:1).

$R_f$ (Pet. ether/EtOAc=60/40): 0.38 $^1$H NMR (500 MHz, DMSO-$d_6$) δ 7.29-7.25 (m, 5H), 7.22 (d, J=7.2 Hz, 1H), 7.17 (d, J=8.0 Hz, 2H), 6.89-6.86 (m, 2H), 6.75 (s, 1H), 6.12 (s, 1H), 5.97-5.95 (m, 1H), 5.67 (d, J=4.7 Hz, 1H), 2.24 (s, 3H, $CH_3$), 2.13 (s, 3H, $CH_3$), $^{13}$C NMR (125 MHz, DMSO-$d_6$) δ 141.50, 139.82, 136.53, 134.97, 133.41, 132.47, 130.73, 129.43, 129.36, 128.54, 128.31, 128.18, 128.02, 125.25, 120.62, 119.20, 118.42, 112.29, 80.03, 78.60, 19.20, 18.95. Representative Peaks of Minor Isomer: $^1$H NMR δ 7.46-7.45 (m), 7.39-7.35 (m), 7.11-6.99 (m), 5.86-5.83 (m), 5.79 (s), 5.62 (d, J=4.6 Hz), 2.32 (s), 2.15 (s), $^{13}$C NMR δ: 141.39, 140.03, 136.86, 135.15, 132.73, 130.85, 130.52, 129.23, 129.12, 128.91, 125.06, 120.45, 119.46, 118.55, 115.38, 76.06, 75.41, 19.27, 19.08. HRMS calculated [M+H]$^+$ for $C_{24}H_{21}ONCl$: 374.1306. found: 374.1314. FTIR (cm$^{-1}$)

3433, 2988, 2254, 1652, 1596, 1490, 1459, 1415, 1282, 1217, 1026, 1003, 926, 876, 820, 744, 663, 624.

Example 16

Synthesis and Characterization of 5-(4-Chlorophenyl)-2,3-difluoro-5H,6aH-benzo[4,5][1,3]oxazino[3,2-a]quinoline (4p)

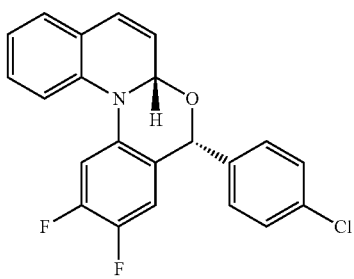

4p

Following the general procedure, treatment of quinoline (0.064 g, 59 μL, 0.50 mmol) and 4-chlorobenzaldehyde (0.105 g, 0.75 mmol) with 4,5-difluoro-2-(trimethylsilyl)phenyl trifluoromethanesulfonate (0.201 g, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=75/25) of the crude reaction mixture afforded 5-(4-chlorophenyl)-2,3-difluoro-5H,6aH-benzo[4,5][1,3]oxazino[3,2-a]quinoline as inseparable mixture of diastereomers as a white solid (0.118 g, 68% yield, dr determined by $^1$H NMR analysis of crude reaction mixture is 10:1).

$R_f$ (Pet. ether/EtOAc=60/40): 0.51 $^1$H NMR (500 MHz, DMSO-$d_6$) δ 7.71-7.67 (m, 1H), 7.45 (dd, $J_1$=8.1 Hz, $J_2$=29.3 Hz, 1H), 7.32-7.31 (m, 3H), 7.28-7.25 (m, 2H), 7.20 (d, J=8.3 Hz, 1H), 7.11 (t, J=9.7 Hz, 1H), 6.95-6.89 (m, 2H), 6.18 (s, 1H), 6.01-5.98 (m, 1H), 5.72 (d, J=4.6 Hz, 1H), $^{13}$C NMR (125 MHz, DMSO-$d_6$) δ 148.43 (dd, $J_1$=14.2 Hz, $J_2$=246.4 Hz), 148.32 (dd, $J_1$=13.6 Hz, $J_2$=245.2 Hz), 140.44, 139.05, 135.48 (m), 132.83, 130.63 (m), 129.60, 129.36, 128.67, 128.54, 128.13, 120.76, 120.06, 118.44, 116.06 (d, J=18.5 Hz), 114.07 (d, J=18.5 Hz), 112.25, 80.08, 78.08 Representative Peaks of Minor Isomer: $^1$H NMR δ 7.80-7.77 (m), 5.89-5.87 (m), 5.87 (s), 5.61 (d, J=4.3 Hz), $^{13}$C NMR δ: 141.05, 138.48, 133.05, 128.08, 120.58, 118.54, 76.06, 75.00. HRMS calculated [M+H]$^+$ for $C_{22}H_{15}ONF_2Cl$: 382.0805. found: 382.0812. FTIR (cm$^{-1}$) 3745, 3009, 1648, 1593, 1572, 1491, 1451, 1418, 1283, 1216, 1153, 1119, 1045, 1010, 960, 924, 875, 841, 807, 769, 741, 696, 658.

Example 17

Synthesis and Characterization of 8-(4-Chlorophenyl)-6aH,8H-[1,3]dioxolo[4″,5″:4′,5′]benzo[1′,2′:4,5][1,3]oxazino[3,2-a]quinoline (4q)

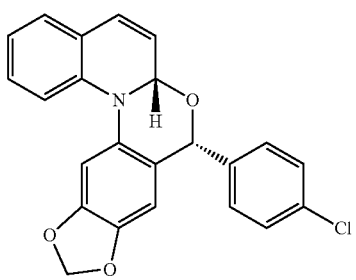

4q

Following the general procedure, treatment of quinoline (0.064 g, 59 μL, 0.50 mmol) and 4-chlorobenzaldehyde (0.105 g, 0.75 mmol) with 6-(trimethylsilyl)benzo[d][1,3]dioxol-5-yl trifluoromethanesulfonate (0.205 g, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=70/30) of the crude reaction mixture afforded 8-(4-chlorophenyl)-6aH,8H [1,3]dioxolo[4″,5″:4′,5′]benzo[1′,2′:4,5][1,3]oxazino[3,2-a]quinoline as inseparable mixture of diastereomers as a white solid (0.171 g, 88% yield, dr determined by $^1$H NMR analysis of crude reaction mixture is >20:1).

$R_f$ (Pet. ether/EtOAc=60/40): 0.38 $^1$H NMR (500 MHz, DMSO-$d_6$) δ 7.29-7.27 (m, 3H), 7.25-7.20 (m, 2H), 7.17 (d, J=8.5 Hz, 2H), 7.08 (s, 1H), 6.91-6.88 (m, 2H), 6.55 (s, 1H), 6.09-6.07 (m, 1H), 6.03 (d, J=9.4 Hz, 2H), 5.99-5.96 (m, 1H), 5.64 (d, J=5.0 Hz, 1H), $^{13}$C NMR (125 MHz, DMSO-$d_6$) δ 146.05, 145.10, 141.43, 139.90, 132.49, 129.39, 129.24, 128.52, 128.36, 127.99, 126.59, 120.77, 119.39, 118.61, 112.54, 106.54, 105.36, 101.48, 80.02, 78.42, HRMS calculated [M+H]$^+$ for $C_{23}H_{17}O_3NCl$: 390.0891. found: 390.0899.

FTIR (cm$^{-1}$) 3395, 2998, 2895, 1648, 1599, 1481, 1430, 1295, 1243, 1215, 1190, 1119, 1089, 1031, 935, 824, 741, 664, 629.

Example 18

Synthesis and Characterization of 5-Phenyl-5H,6aH-naphtho[2',1':4,5][1,3]oxazino[3,2-a]quinoline (4r)

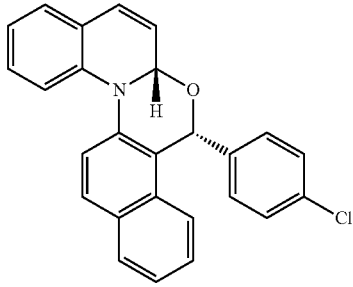

4r

Following the general procedure, treatment of quinoline (0.064 g, 59 μL, 0.50 mmol) and 4-chlorobenzaldehyde (0.105 g, 0.75 mmol) with 2-(trimethylsilyl)naphthalen-1-yl trifluoromethanesulfonate (0.209 g, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. Ether/EtOAc=75/25) of the crude reaction mixture afforded 5-phenyl-5H,6aHnaphtho[2',1':4,5][1,3]oxazino[3,2-a]quinoline as a yellow solid (0.133 g, 67% yield, dr determined by $^1$H NMR analysis of crude reaction mixture is >20:1).

Rf (Pet. ether/EtOAc=60/40): 0.49 $^1$H NMR (400 MHz, DMSO-d$_6$) δ 8.01-7.96 (m, 2H), 7.72 (d, J=8.7 Hz, 1H), 7.42-7.36 (m, 3H), 7.30-7.20 (m, 5H), 7.14 (d, J=2.5 Hz, 2H), 6.88 (d, J=9.7 Hz, 2H), 6.46 (s, 1H), 5.72-5.68 (m, 1H), 5.58 (d, J=4.4 Hz, 1H), $^{13}$C NMR (100 MHz, DMSO-d$_6$) δ 141.45, 139.37, 137.64, 132.68, 130.75, 130.67, 130.56, 129.11, 128.87, 128.63, 128.58, 127.96, 127.64, 126.41, 125.10, 124.24, 124.03, 123.73, 121.09, 120.10, 118.63, 112.76, 74.50, HRMS calculated [M+H]$^+$ for C$_{26}$H$_{19}$ONCl: 396.1150. found: 396.1163. FTIR (cm$^{-1}$) 3390, 3012, 2962, 1647, 1597, 1570, 1490, 1459, 1415, 1347, 1287, 1214, 1176, 1090, 1005, 955, 829, 741, 662, 630.

Example 19

Synthesis and Characterization of 5,5-Diphenyl-5H,6aH-benzo[4,5][1,3]oxazino[3,2-a]quinoline (7a)

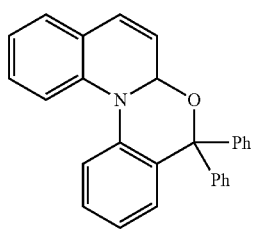

7a

Following the general procedure, treatment of quinoline (0.064 g, 59 μL, 0.50 mmol) and benzophenone (0.136 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=95/05) of the crude reaction mixture afforded 5,5-diphenyl-5H,6aH-benzo[4,5][1,3]oxazino[3,2-a]quinoline as a yellow solid (0.105g, 54% yield).

R$_f$ (Pet. ether/EtOAc=80/20): 0.85 $^1$H NMR (500 MHz, DMSO-d$_6$) δ 7.55 (d, J=7.7 Hz, 1H), 7.42-7.38 (m, 4H), 7.29-7.28 (m, 3H), 7.23-7.11 (m, 7H), 7.04-7.03 (m, 2H), 6.92-6.89 (m, 2H), 5.81-5.77 (m, 1H), 5.33 (d, J=4.4 Hz, 1H), $^{13}$C NMR (125 MHz, DMSO-d$_6$) δ 146.46, 144.81, 139.37, 138.88, 134.36, 130.69, 129.30, 128.86, 128.77, 128.05, 127.78, 127.34, 127.08, 126.83, 125.52, 124.24, 120.76, 119.69, 118.40, 112.13, 84.65, 77.18, HRMS calculated [M+H]$^+$ for C$_{28}$H$_{22}$ON: 388.1696. found: 388.1701. FTIR (cm$^{-1}$) 3012, 1656, 1599, 1489, 1457, 1369, 1215, 1029, 859, 817, 741, 665, 626.

Example 20

Synthesis and Characterization of 6aH-Spiro[benzo[4,5][1,3]oxazino[3,2-a]quinoline-5,1'-cyclohexane]-2',5'-dien-4'-one (7b)

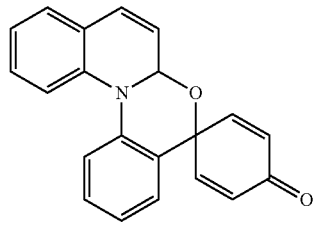

7b

Following the general procedure, treatment of quinoline (0.064 g, 59 μL, 0.50 mmol) and benzoquinone (0.082 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. Ether/EtOAc=85/15) of the crude reaction mixture afforded 6aH-spiro[benzo[4,5][1,3]oxazino[3,2-a]quinoline-5,1'-cyclohexane]-2',5'-dien-4'-one as a white solid (0.124 g, 59% yield).

R$_f$ (Pet. ether/EtOAc=80/20): 0.73 $^1$H NMR (500 MHz, DMSO-d$_6$) δ 7.62 (d, J=7.9 Hz, 1H), 7.52-7.50 (m, 1H), 7.45 (t, J=7.3 Hz, 1H), 7.32 (d, J=7.2 Hz, 1H), 7.28-7.22 (m, 3H), 7.12 (t, J=7.8 Hz, 1H), 6.98 (t, J=9.4 Hz, 1H), 6.93 (t, J=6.7 Hz, 1H), 6.50-6.48 (m, 1H), 6.26 (d, J=10.0 Hz, 1H), 6.09 (d, J=9.9 Hz, 1H), 6.02-6.00 (m, 1H), 5.95 (d, J=4.5 Hz, 1H), $^{13}$C NMR (125 MHz, DMSO-d$_6$) δ 185.05, 150.78, 147.20, 139.68, 138.60, 129.53, 129.07, 128.20, 127.98, 127.92, 127.79, 126.51, 125.75, 125.57, 125.49, 120.58, 119.97, 117.98, 112.34, 77.36, 74.08, HRMS calculated [M+H]$^+$ for $C_{21}H_{16}O_2N$: 314.1176. found: 314.1184. FTIR (cm$^{-1}$) 3748, 3020, 1652, 1593, 1490, 1451, 1414, 1287, 1214, 1090, 1008, 928, 832, 748, 668.

Example 21

Synthesis and Characterization of Phenyl(5-phenyl-5H,6aH-benzo[4,5][1,3]oxazino[3,2-a]quinolin-5-yl)methanone (7c)

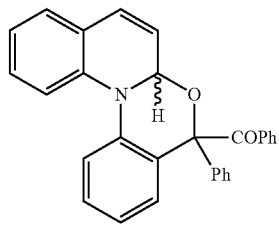

7c

Following the general procedure, treatment of quinoline (0.064 g, 59 μL, 0.50 mmol) and benzyl (0.158 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=95/05) of the crude reaction mixture afforded phenyl(5-phenyl-5H,6aH-benzo[4,5][1,3]oxazino[3,2-a]quinolin-5-yl)-methanone as inseparable mixture of diastereomers as a yellow solid (0.131 g, 63% yield, dr determined by $^1$H NMR analysis of crude reaction mixture is >20:1).

R$_f$ (Pet. ether/EtOAc=80/20): 0.83 $^1$H NMR (400 MHz, DMSO-d$_6$) δ 7.81 (d, J=7.4 Hz, 2H), 7.55-7.49 (m, 2H), 7.41-7.32 (m, 5H), 7.29-7.16 (m, 8H), 7.00-6.91 (m, 2H), 5.65-5.55 (m, 2H), $^{13}$C NMR (100 MHz, DMSO-d$_6$) δ 197.06, 142.49, 139.05, 137.83, 134.08, 132.76, 131.84, 131.74, 130.59, 129.59, 129.55, 129.46, 128.74, 128.24, 128.02, 126.78, 125.49, 124.72, 124.08, 120.70, 120.02, 117.56, 112.42, 86.99, 79.05. Representative Peaks of Minor Isomer: $^1$H NMR δ 7.67 (d, J=8.1 Hz), 7.45-7.43 (m), 6.86 (d, J=9.6 Hz), 5.89-5.85 (m), $^{13}$C NMR δ: 198.60, 142.07, 139.35, 138.55, 135.04, 132.38, 130.00, 129.94, 127.75, 127.44, 129.41, 129.38, 128.88, 128.09, 125.20, 124.77, 120.24, 119.88, 111.75, 88.62, 78.32. HRMS calculated [M+H]$^+$ for $C_{29}H_{22}O_2N$: 416.1645. found: 416.1653. FTIR (cm$^{-1}$) 3390, 3058, 1933, 1733, 1653, 1620, 1595, 1573, 1499, 1428, 1370, 1314, 1257, 1218, 1119, 1090, 1034, 942, 804, 773, 740, 663.

Example 22

Synthesis and Characterization of Thiophen-2-yl(5-(thiophen-2-yl)-5H,6aH-benzo[4,5][1,3]oxazino[3,2-a]quinolin-5-yl)methanone (7d)

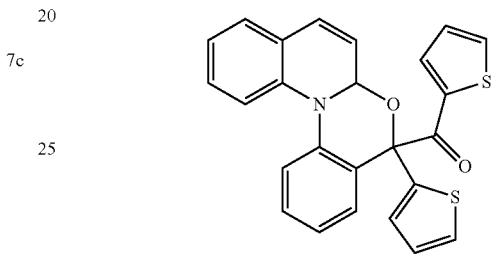

7d

Following the general procedure, treatment of quinoline (0.064 g, 59 μL, 0.50 mmol) and 1,2-di(thiophen-2-yl)ethane-1,2-dione (0.166 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=95/05) of the crude reaction mixture afforded thiophen-2-yl(5-(thiophen-2-yl)-5H, 6aH-benzo[4,5][1,3]oxazino[3,2-a]quinolin-5-yl)methanone as inseparable mixture of diastereomers as a yellow solid (0.120 g, 56% yield, dr determined by $^1$H NMR analysis of crude reaction mixture is 1:1).

R$_f$ (Pet. ether/EtOAc=80/20): 0.68 $^1$H NMR (400 MHz, DMSO-d$_6$) δ 7.74 (d, J=4.5 Hz, 1H), 7.66-7.64 (m, 1H), 7.54 (d, J=8.2 Hz, 1H), 7.51-7.49 (m, 1H), 7.44-7.39 (m, 1H), 7.36 (d, J=4.6 Hz, 1H), 7.34-7.31 (m, 1H), 7.29-7.26 (m, 1H), 7.22-7.14 (m, 2H), 7.07-7.01 (m, 2H), 6.97-6.92 (m, 2H), 6.80-6.78 (m, 1H), 6.01-5.98 (m, 1H), 5.76 (d, J=5.0 Hz, 1H), $^{13}$C NMR (100 MHz, DMSO-d$_6$) δ 189.21, 146.63, 138.56, 138.40, 137.90, 136.61, 135.50, 131.58, 129.55, 129.52, 128.83, 128.42, 128.17, 127.85, 127.34, 126.57, 125.28, 125.02, 124.74, 120.43, 120.20, 117.38, 112.50, 86.43, 78.20. Representative Peaks of Minor Isomer: $^1$H NMR δ 8.02 (d, J=4.3 Hz), 7.94 (d, J=3.2 Hz), 7.61 (d, J=7.7 Hz), 6.86-6.83 (m), 5.93-5.90 (m), 5.71 (d, J=5.0 Hz), $^{13}$C NMR δ: 189.03, 146.01, 138.82, 138.23, 137.96, 136.46, 136.23, 130.72, 129.67, 129.49, 128.61, 128.37, 127.63, 126.88, 126.29, 124.63, 124.10, 120.60, 120.04, 117.14, 111.96, 84.73, 80.00. HRMS calculated [M+H]$^+$ for $C_{25}H_{18}O_2NS_2$:

Example 23

Synthesis and Characterization of 5-Phenyl-5H,6aH-benzo[4,5][1,3]oxazino[3,2-a]quinoline-5-carboxylate (7e)

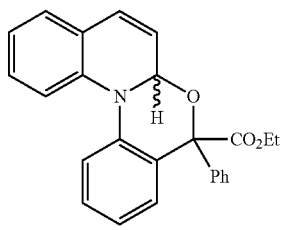

7e

Following the general procedure, treatment of quinoline (0.064 g, 59 μL, 0.50 mmol) and ethyl 2-oxo-2-phenylacetate (0.134 g, 119 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=90/10) of the crude reaction mixture afforded ethyl 5-phenyl-5H,6aHbenzo[4,5][1,3]oxazino[3,2-a]quinoline-5-carboxylate as a white solid (0.147 g, 77% yield, dr determined by $^1$H NMR analysis of crude reaction mixture is >20:1).

$R_f$ (Pet. ether/EtOAc=80/20): 0.80 $^1$H NMR (500 MHz, DMSO-$d_6$) δ 7.59-7.55 (m, 2H), 7.49-7.45 (m, 1H), 7.30-7.20 (m, 7H), 7.06-7.04 (m, 2H), 6.95 (d, J=9.6 Hz, 1H), 6.91-6.87 (m, 1H), 6.06-6.02 (m, 1H), 5.83 (t, J=5.1 Hz, 1H), 4.31 (q, $J_1$=6.8 Hz, $J_2$=13.3 Hz, $J_3$=20.2 Hz, 2H), 1.27 (t, J=7.1 Hz, 3H), $^{13}$C NMR (125 MHz, DMSO-$d_6$) δ 171.33, 141.67, 139.58, 138.99, 130.22, 130.14, 129.42, 128.99, 128.22, 127.65, 126.79, 125.07, 124.64, 120.75, 119.86, 117.97, 112.18, 83.96, 79.29, 61.90, 13.89. HRMS calculated [M+H]$^+$ for $C_{25}H_{22}O_3N$: 384.1594. found: 384.1599. FTIR (cm$^{-1}$) 3398, 2996, 1681, 1596, 1489, 1449, 1417, 1278, 1216, 1182, 1123, 1028, 969, 901, 852, 821, 742, 698, 660.

Example 24

Synthesis and Characterization of 6-(p-Tolyl)-4bH,6H-benzo[4,5][1,3]oxazino[2,3-a]isoquinoline (9a)

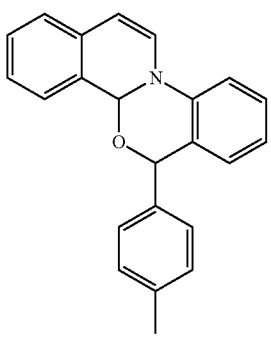

9a

Following the general procedure, treatment of isoquinoline (0.064 g, 59 μL, 0.50 mmol) and 4-methylbenzaldehyde (0.090 g, 85 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=90/10) of the crude reaction mixture afforded 6-(p-tolyl)-4bH,6Hbenzo[4,5][1,3]oxazino[2,3-a]isoquinoline as inseparable mixture of diastereomers as a yellow solid (0.130 g, 80% yield, dr determined by $^1$H NMR analysis of crude reaction mixture is 3:2).

$R_f$ (Pet. ether/EtOAc=80/20): 0.68 $^1$H NMR (500 MHz, DMSO-$d_6$) δ 7.40-7.35 (m, 2H), 7.32-7.25 (m, 3H), 7.18 (d, J=7.9 Hz, 2H), 7.15-7.08 (m, 4H), 6.96 (d, J=7.3 Hz, 1H), 6.75 (d, J=7.6 Hz, 1H), 6.49 (s, 1H), 6.37 (s, 1H), 5.74 (d, J=7.4 Hz, 1H), 2.26 (s, 3H, $CH_3$), $^{13}$C NMR (125 MHz, DMSO-$d_6$) δ 140.31, 138.85, 137.26, 131.43, 129.84, 129.06, 128.93, 128.85, 128.49, 128.05, 127.60, 127.30, 125.33, 125.22, 123.57, 122.59, 117.40, 99.11, 82.73, 80.20, 20.68. Representative Peaks of Minor Isomer: $^1$H NMR δ 7.47 (d, J=8.2 Hz), 7.03 (d, J=10.0 Hz), 6.92 (d, J=7.6 Hz), 6.08 (s), 5.95 (s), 5.70 (d, J=7.7 Hz), 2.35 (s). $^{13}$C NMR δ: 140.09, 139.41, 137.31, 130.09, 129.00, 128.14, 125.61, 125.33, 125.31, 123.65, 121.67, 116.53, 99.03, 77.20, 75.97, 20.59. HRMS calculated [M+H]$^+$ for $C_{23}H_{20}ON$: 326.1539. found: 428.0773. found: 428.0775. FTIR (cm$^{-1}$) 3397, 2991, 1732, 1651, 1593, 1487, 1446, 1280, 1217, 1118, 1052, 1027, 962, 896, 824, 769, 741, 663.

326.1541. FTIR (cm$^{-1}$) 3018, 1730, 1600, 1489, 1456, 1372, 1243, 1217, 1102, 1043, 936, 741, 665, 632.

Example 25

Synthesis and Characterization of 6-(4-Bromophenyl)-4bH,6H-benzo[4,5][1,3]oxazino[2,3-a]isoquinoline (9b)

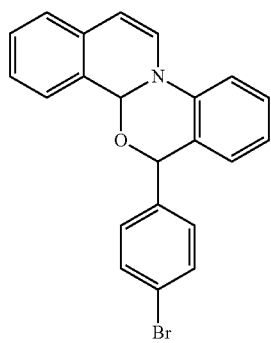

9b

Following the general procedure, treatment of isoquinoline (0.129 g, 120 μL, 1.0 mmol) and 4-bromobenzaldehyde (0.278 g, 1.5 mmol) with 2-(trimethylsilyl)phenyl trifluoromethane sulfonate (0.308 g, 292 μL, 1.2 mmol) in the presence of KF (0.140 g, 2.4 mmol) and 18-crown-6 (0.634 g, 2.4 mmol) in THF (4.0 mL) at −10° C. to room temperature for 12 hrs followed by flash column chromatography (Pet. ether/EtOAc=93/07) of the crude reaction mixture afforded 6-(4-bromophenyl)-4bH,6H-benzo[4,5][1,3]oxazino[2,3-a]isoquinoline as inseparable mixture of diastereomers as a yellow solid (0.314 g, 82% yield, dr determined by $^1$H NMR analysis of crude reaction mixture is 3:2).

$R_f$ (Pet. ether/EtOAc=80/20): 0.78 $^1$H NMR (500 MHz, DMSO-$d_6$) δ 7.67 (d, J=8.2 Hz, 1H), 7.51 (d, J=8.2 Hz, 2H), 7.36 (d, J=7.5 Hz, 2H), 7.25 (d, J=8.5 Hz, 3H), 7.12-7.10 (m, 3H), 6.98 (d, J=7.2 Hz, 1H), 6.77 (d, J=7.6 Hz, 1H), 6.48 (s, 1H), 6.41 (s, 1H), 5.75 (d, J=7.6 Hz, 1H), $^{13}$C NMR (125 MHz, DMSO-$d_6$) δ 141.29, 140.31, 131.41, 131.34, 131.16, 130.26, 129.82, 129.17, 128.58, 127.84, 127.26, 125.34, 125.31, 123.66, 122.82, 121.91, 121.19, 117.68, 99.25, 82.68, 79.58. Representative Peaks of Minor Isomer: $^1$H NMR δ 7.47 (d, J=8.3 Hz), 7.32-7.28 (m), 7.03 (d, J=7.6 Hz), 6.83 (d, J=7.6 Hz), 6.05 (s), 5.97 (s), 5.70 (d, J=7.5 Hz), $^{13}$C NMR δ: 141.57, 140.17, 129.43, 129.02, 128.80, 128.29, 128.16, 127.76, 125.40, 124.76, 123.73, 121.54, 116.83, 99.13, 77.46, 75.33. HRMS calculated [M+H]$^+$ for C$_{22}$H$_{17}$ONBr: 390.0488. found: 390.0497. FTIR (cm$^{-1}$) 3395, 2256, 2127, 1658, 1632, 1595, 1485, 1456, 1425, 1397, 1299, 1248, 1218, 998, 934, 877, 824, 768, 659, 622.

Example 26

Synthesis and Characterization of 6-(4-Chlorophenyl)-4bH,6H-benzo[4,5][1,3]oxazino[2,3-a]isoquinoline (9c)

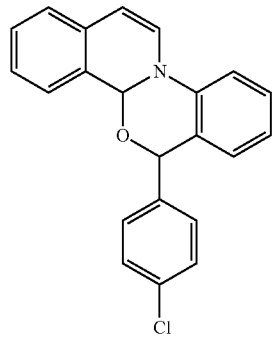

9c

Following the general procedure, treatment of isoquinoline (0.064 g, 59 μL, 0.50 mmol) and 4-chlorobenzaldehyde (0.105 g, 0.75 mmol) with 2-(trimethylsilyl)phenyl trifluoromethane sulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=93/07) of the crude reaction mixture afforded 6-(4-chlorophenyl)-4bH,6H-benzo[4,5][1,3]oxazino[2,3-a]isoquinoline as inseparable mixture of diastereomers as a yellow solid (0.140 g, 81% yield, dr determined by $^1$H NMR analysis of crude reaction mixture is 3:2).

$R_f$ (Pet. ether/EtOAc=80/20): 0.71 $^1$H NMR (500 MHz, DMSO-$d_6$) δ 7.43 (d, J=8.5 Hz, 1H), 7.38 (d, J=8.3 Hz, 3H), 7.31 (d, J=8.3 Hz, 2H), 7.28-7.25 (m, 1H), 7.18 (d, J=7.6 Hz, 1H), 7.15-7.13 (m, 1H), 7.11-7.08 (m, 2H), 6.98 (d, J=7.5 Hz, 1H), 6.77 (d, J=7.7 Hz, 1H), 6.49 (s, 1H), 6.43 (s, 1H), 5.75 (d, J=7.6 Hz, 1H), $^{13}$C NMR (125 MHz, DMSO-$d_6$) δ 140.87, 140.32, 132.60, 131.39, 130.81, 129.91, 1229.15, 128.56, 128.47, 128.40, 127.83, 127.24, 125.35, 125.29, 123.65, 122.80, 117.65, 99.24, 82.68, 74.93. Representative Peaks of Minor Isomer: $^1$H NMR δ 7.52 (d, J=78.4 Hz), 7.48 (d, J=8.2 Hz), 7.04 (d, J=7.2 Hz), 6.83 (d, J=7.5 Hz), 6.05 (s), 5.99 (s), 5.70 (d, J=7.6 Hz), $^{13}$C NMR δ: 141.17, 140.16, 132.83, 129.80, 129.48, 128.99, 128.78, 128.28, 128.14, 127.72, 124.81, 123.71, 121.89, 116.80, 99.13, 77.44, 75.26. HRMS calculated [M+H]$^+$ for C$_{22}$H$_{17}$ONCl: 346.0993. found:

346.0872. FTIR (cm$^{-1}$) 3736, 3019, 1730, 1854, 1601, 1506, 1456, 1373, 1216, 1156, 1043, 931, 846, 741, 667.

Example 27

Synthesis and Characterization of 6-(4-Fluorophenyl)-4bH,6H-benzo[4,5][1,3]oxazino[2,3-a]isoquinoline (9d)

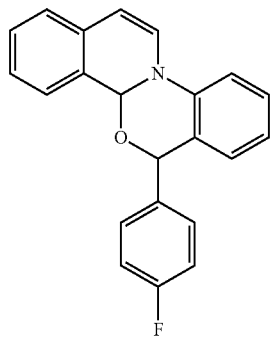

9d

Following the general procedure, treatment of isoquinoline (0.064 g, 59 μL, 0.50 mmol) and 4-fluorobenzaldehyde (0.093 g, 80 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=93/07) of the crude reaction mixture afforded 6-(4-fluorophenyl)-4bH,6H-benzo[4,5][1,3]oxazino[2,3-a]isoquinoline as inseparable mixture of diastereomers as a yellow solid (0.151 g, 92% yield, dr determined by $^1$H NMR analysis of crude reaction mixture is 3:2).

R$_f$ (Pet. ether/EtOAc=80/20): 0.63 $_1$H NMR (500 MHz, DMSO-d$_6$) δ 7.19-7.43 (m, 1H), 7.37 (d, J=8.2 Hz, 2H), 7.34-7.32 (m, 2H), 7.28-7.26 (m, 1H), 7.19-7.13 (m, 2H), 7.12-7.07 (m, 3H), 7.00-6.96 (m, 1H), 6.76 (d, J=7.6 Hz, 1H), 6.50 (s, 1H), 6.43 (s, 1H), 5.74 (d, J=7.6 Hz, 1H), $_{13}$C NMR (125 MHz, DMSO-d$_6$) δ 161.75 (d, J=243.8 Hz), 140.35, 138.13 (d, J=2.7 Hz), 131.40, 131.10 (d, J=8.5 Hz), 130.18, 130.10, 129.14, 128.54, 127.78, 127.28, 125.41, 125.28, 123.62, 122.77, 117.62, 116.75, 115.18 (d, J=21.5 Hz), 99.20, 82.68, 79.47. Representative Peaks of Minor Isomer: $_1$H NMR δ 7.58-7.55 (m), 7.05-7.03 (m), 6.82 (d, J=7.5 Hz), 6.06 (s), 6.00 (s), 5.70 (d, J=7.6 Hz), $_{13}$C NMR δ: 140.14, 138.66 (d, J=2.9 Hz), 131.42, 129.86, 129.78, 129.47, 128.97, 128.81, 128.18 (d, J=8.2 Hz), 127.66, 125.45, 125.37, 125.13, 123.70, 121.86, 115.25 (d, J=21.2 Hz), 99.10, 77.24, 75.30. HRMS calculated [M+H]$^+$ for C$_{22}$H$_{17}$ONF: 330.1289. found: 330.1297. FTIR (cm$_{-1}$) 3014, 1653, 1593, 1491, 1451, 1417, 1285, 1216, 1119, 1046, 1001, 922, 878, 839, 769, 741, 664.

Example 28

Synthesis and Characterization of 6-(3-Bromophenyl)-4bH,6H-benzo[4,5][1,3]oxazino[2,3-a]isoquinoline (9e)

9e

Following the general procedure, treatment of isoquinoline (0.064 g, 59 μL, 0.50 mmol) and 3-bromobenzaldehyde (0.139 g, 884, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=93/07) of the crude reaction mixture afforded 6-(3-bromophenyl)-4bH,6H-benzo[4,5][1,3]oxazino[2,3-a]isoquinoline as inseparable mixture of diastereomers as a yellow solid (0.121 g, 62% yield, dr determined by $^1$H NMR analysis of crude reaction mixture is 3:2).

R$_f$ (Pet. ether/EtOAc=80/20): 0.61 $_1$H NMR (400 MHz, DMSO-d$_6$) δ 7.62-7.59 (m, 1H), 7.49-7.43 (m, 2H), 7.41-7.35 (m, 2H), 7.33-7.31 (m, 2H), 7.29-7.25 (m, 1H), 7.19-7.16 (m, 1H), 7.14-7.08 (m, 2H), 6.99 (d, J=7.1 Hz, 1H), 6.81 (d, J=7.6 Hz, 1H), 6.48 (s, 1H), 6.43 (s, 1H), 5.76 (d, J=7.4 Hz, 1H), $_{13}$C NMR (100F MHz, DMSO-d$_6$) δ 144.60, 140.32, 131.37, 130.95, 130.65, 130.53, 129.23, 129.18, 128.57, 127.90, 127.60, 127.23, 125.32, 125.28, 123.68, 122.89, 121.52, 117.78, 99.28, 82.65, 79.36. Representative Peaks of Minor Isomer: $_1$H NMR δ 7.06-7.04 (m), 6.84 (d, J=7.9 Hz), 6.08 (s), 6.00 (s), 5.71 (d, J=7.7 Hz), $_{13}$C NMR δ: 144.86, 140.17, 131.64, 131.40, 130.73, 129.80, 129.02, 128.75, 128.35, 128.12, 127.99, 125.40, 124.57, 123.75, 121.94, 121.83, 116.84, 99.18, 77.63, and 75.26. HRMS calculated [M+H]$^+$ for $C_{22}H_{17}ONBr$: 390.0488. found: 390.0499. FTIR (cm$^{-1}$) 3865, 3748, 3019, 1730, 1600, 1489, 1455, 1372, 1218, 1043, 934, 769, 741, 666, 631.

Example 29

Synthesis and Characterization of 6-(2-Fluorophenyl)-4bH,6H-benzo[4,5][1,3]oxazino[2,3-a]isoquinoline (9f)

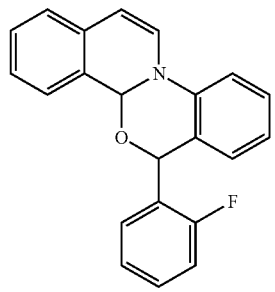

9f

Following the general procedure, treatment of isoquinoline (00.064 g, 59 μL, 0.50 mmol) and 2-fluorobenzaldehyde (0.095 g, 79 μL, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=93/07) of the crude reaction mixture afforded 6-(2-fluorophenyl)-4bH,6H-benzo[4,5][1,3]oxazino[2,3-a]isoquinoline as inseparable mixture of diastereomers as a yellow solid (0.105 g, 64% yield, dr determined by $^1$H NMR analysis of crude reaction mixture is 3:1).

$R_f$ (Pet. ether/EtOAc=80/20): 0.65 $^1$H NMR (500 MHz, DMSO-d$_6$) δ 7.48-7.46 (m, 1H), 7.41 (d, J=7.6 Hz, 1H), 7.37-7.34 (m, 1H), 7.32-7.31 (m, 1H), 7.29-7.26 (m, 2H), 7.18 (d, J=7.9 Hz, 2H), 7.14 (d, J=8.2 Hz, 1H), 7.10 (d, J=7.2 Hz, 1H), 7.07-7.06 (m, 1H), 7.01-6.97 (m, 1H), 6.91 (d, J=7.9 Hz, 1H), 6.73 (s, 1H), 6.53 (s, 1H), 5.77 (d, J=7.6 Hz, 1H), $^{13}$C NMR (125 MHz, DMSO-d$_6$) δ 160.29 (d, J=247.3 Hz), 140.63, 131.42, 130.09 (d, J=8.5 Hz), 129.85, 129.81, 129.08 (d, J=4.2 Hz), 128.62, 128.57, 127.79, 127.75, 126.46, 125.27 (d, J=9.1 Hz), 124.42 (d, J=3.9 Hz), 123.60, 122.85, 117.57, 115.56 (d, J=21.6 Hz), 99.22, 82.89, 74.32. Representative Peaks of Minor Isomer: $^{11}$H NMR δ 7.24-7.21 (m), 6.29 (s), 6.16 (s), 5.74 (d, J=7.6 Hz), $^{13}$C NMR δ: 160.44 (d, J=248.7 Hz), 140.50, 131.32 (d, J=3.6 Hz), 130.49 (d, J=8.2 Hz), 129.88, 128.99, 128.92, 128.75, 128.25, 127.67, 123.97 (d, J=2.7 Hz), 123.71, 122.03, 116.72, 115.70 (d, J=21.4 Hz), 99.13, 77.56, 70.56. HRMS calculated [M+H]$^+$ for $C_{22}H_{17}ONF$: 330.1289. found: 330.1300. FTIR (cm$^{-1}$) 3015, 1654, 1601, 1490, 1456, 1216, 1029, 934, 740, 666, 629.

Example 30

Synthesis and Characterization of 6-(3,4-Dichlorophenyl)-4bH,6H-benzo[4,5][1,3]oxazino[2,3-a]isoquinoline (9g)

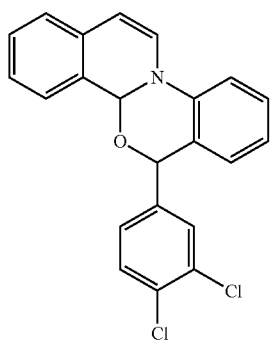

9g

Following the general procedure, treatment of isoquinoline (0.064 g, 59 μL, 0.50 mmol) and 3,4-dichlorobenzaldehyde (0.130 g, 0.75 mmol) with 2-(trimethylsilyl)phenyl trifluoromethanesulfonate (0.179 g, 146 μL, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=93/07) of the crude reaction mixture afforded 6-(3,4-dichlorophenyl)-4bH,6H-benzo[4,5][1,3]oxazino[2,3-a]isoquinoline as inseparable mixture of diastereomers as a yellow solid (0.146 g, 77% yield, dr determined by $^1$H NMR analysis of crude reaction mixture is 1:1).

$R_f$ (Pet. ether/EtOAc=80/20): 0.73 $^1$H NMR (500 MHz, DMSO-d$_6$) δ 7.56-7.54 (m, 2H), 7.41-7.34 (m, 2H), 7.32-7.24 (m, 3H), 7.18-7.15 (m, 1H), 7.13-7.08 (m, 2H), 6.99 (d, J=7.7 Hz, 1H), 6.82 (d, J=7.7 Hz, 1H), 6.47 (s, 1H), 6.44 (s, 1H), 5.76 (d, J=7.5 Hz, 1H), $^{13}$C NMR (125 MHz, DMSO-d$_6$) δ 142.96, 140.30, 131.37, 131.04, 130.71, 129.87, 129.72, 129.22, 128.87, 128.60, 128.25, 128.01, 127.22, 125.34, 125.20, 123.72, 122.93, 117.82, 99.33, 82.69, 78.77. Representative Peaks of Minor Isomer: $^1$H NMR δ 7.70 (d, J=8.4 Hz), 7.62 (d, J=1.8 Hz), 7.47 (d, J=8.3 Hz), 7.04 (d, J=7.2 Hz), 6.86 (d, J=7.6 Hz), 6.08 (s), 5.99 (s), 5.71 (d, J=7.5 Hz), $^{13}$C NMR δ: 143.15, 140.24, 131.25, 130.95, 130.90, 129.16, 129.04, 128.74, 128.44, 128.10, 127.86, 125.40, 124.32, 122.03, 116.98, 99.20, 77.70, 74.69. HRMS calculated [M+H]$^+$ for $C_{22}H_{16}ONCl_2$: 380.0603. found: 380.0611.

FTIR (cm$^{-1}$) 3744, 3017, 1653, 1593, 1491, 1456, 1290, 1216, 1033, 928, 768, 741, 667.

Example 31

Synthesis and Characterization of 8,9-Dimethyl-6-phenyl-4bH,6H-benzo[4,5][1,3]oxazino[2,3-a]isoquinoline (9h)

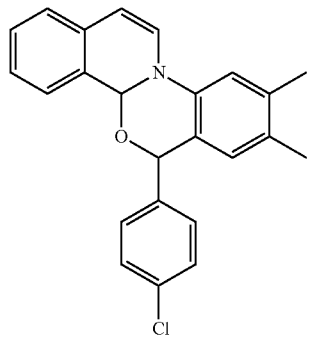

9h

Following the general procedure, treatment of isoquinoline (0.064 g, 59 µL, 0.50 mmol) and 4-chlorobenzaldehyde (0.105 g, 0.75 mmol) with 4,5-dimethyl-2-(trimethylsilyl) phenyl trifluoromethanesulfonate (0.196 g, 0.60 mmol) in the presence of KF (0.070 g, 1.2 mmol) and 18-crown-6 (0.317 g, 1.2 mmol) in THF (2.0 mL) at −10° C. to room temperature for 12 hrs followed by flash column chromatography (Pet. ether/EtOAc=90/10) of the crude reaction mixture afforded 8,9-dimethyl-6-phenyl-4bH,6H-benzo[4,5][1,3]oxazino[2,3-a]isoquinoline as inseparable mixture of diastereomers as a yellow solid (0.127 g, 68% yield, dr determined by $^1$H NMR analysis of crude reaction mixture is 3:2).

$R_f$ (Pet. ether/EtOAc=80/20): 0.61 $^1$H NMR (500 MHz, DMSO-$d_6$) δ 7.50 (d, J=7.7 Hz, 1H), 7.42 (d, J=8.2 Hz, 1H), 7.35 (d, J=6.6 Hz, 2H), 7.30-7.29 (m, 2H), 7.15-7.11 (m, 3H), 7.04-7.03 (m, 1H), 6.51 (s, 1H), 6.39 (s, 1H), 6.32 (s, 1H), 5.71 (d, J=7.6 Hz, 1H), 2.21 (s, 3H, CH$_3$), 2.05 (s, 3H, CH$_3$), $^{13}$C NMR (125 MHz, DMSO-$d_6$) δ 141.10, 138.12, 136.09, 132.50, 131.52, 130.95, 130.76, 130.14, 129.87, 129.03, 128.56, 128.32, 127.58, 126.78, 125.24, 125.07, 123.53, 118.57, 98.65, 87.20, 79.26, 19.21, 18.68. Representative Peaks of Minor Isomer: $^1$H NMR δ 7.26-7.24 (m), 7.14-7.07 (m), 6.80 (d, J=7.5 Hz), 6.77 (s), 6.03 (s), 5.88 (s), 5.66 (d, J=7.7 Hz), 2.28 (s), 2.16 (s), $^{13}$C NMR δ: 141.33, 138.04, 136.57, 132.76, 131.55, 130.09, 129.15, 128.87, 128.49, 128.40, 127.77, 127.39, 125.15, 123.58, 122.19, 117.67, 98.48, 77.37, 75.12, 19.40, 18.65. HRMS calculated [M+H]$^+$ for C$_{24}$H$_{21}$ONCl: 374.1306. found: 374.1316. FTIR (cm$^{-1}$) 3746, 3013, 1651, 1594, 1492, 1451, 1421, 1286, 1216, 1118, 1042, 999, 924, 854, 769, 741, 664.

Example 32

Anti-Malarial Screening Protocol Followed—

*Plasmodium* Culture:

*Plasmodium falciparum* (3D7; Malaria Research and Reference Reagent Resource Center ID NO: MRA-102) is cultured in the laboratory as per standard protocols. Briefly, *P. falciparum* is cultured using 2% hematocrit washed RBCs, separated from freshly collected human blood, in Roswell Park Memorial Institute (RPMI) medium containing glutamine, sodium bicarbonate and antibiotics. Parasites are synchronized using either 5% sorbitol treatment or by enriching late stage parasites using a 70% percol cushion.

Setting Up the Anti-Malarial Screen:

200 µls of the diluted parasite culture at 2% parasitemia and 2% hematocrit, is added to each well in a 96 well plate pre-seeded with the compound of interest at the required concentration. In general, compounds being screened for the first time are tested at a single concentration of 10 µM to detect any effect they may have on parasite growth. The master stocks and dilutions of the compounds are prepared in cell culture grade DMSO. NOTE: DMSO only treatment control is done and the results are used for normalizing the data obtained from compound treatment. All compounds are plated in triplicates. Each 96 well plate also includes negative control (compound untreated culture) and positive control (standard anti-malarial treated culture). Standard anti-malarials used are chloroquine, artemisinine and atovaquone, each at 1 µM concentration. After plating, the culture is incubated in standard growth condition for 60 hours, after which the cultures are processed for testing the effect of compounds on parasite growth as given below.

Estimating Parasite Growth by SybrGreen Staining:

We have standardized a modified SybrGreen dye based staining protocol (Plouffe D et. al. in *Proc Natl Acad Sci*, 2008, 105(26), 9059-64) for estimating parasite growth. SybrGreen dye binds to DNA and only the DNA bound dye gives a specific fluorescence emission (520 nM) when excited (498 nM). Since only the parasites have DNA (as RBCs are devoid of nucleus), the SybrGreen signal is a direct indictor of parasite growth. We have standardized a plate reader based read out assay for quantifying relative parasite growth (or conversely % inhibition of growth) in untreated, standard anti-malarial treated and test molecules treated *P. falciparum* cultures. 25 µl of 10× staining solution (0.5% Triton X100 & 10× SybrGreen dye in phosphate buffered saline) is added to each sample in 96 well plate, mixed and incubated for 30 min before taking readings.

Data obtained is then tabulated to compare parasite growth between untreated, standard anti-malarial treated and compound treated parasite cultures. Compounds showing greater than 80% reduction in parasite growth are selected from this primary screening for carrying out dose response analysis using the respective test molecules from 10 µM to 1 nM. Data from this experiment is used for the calculation of IC$_{50}$ values for the respective test molecules.

Figure 2:
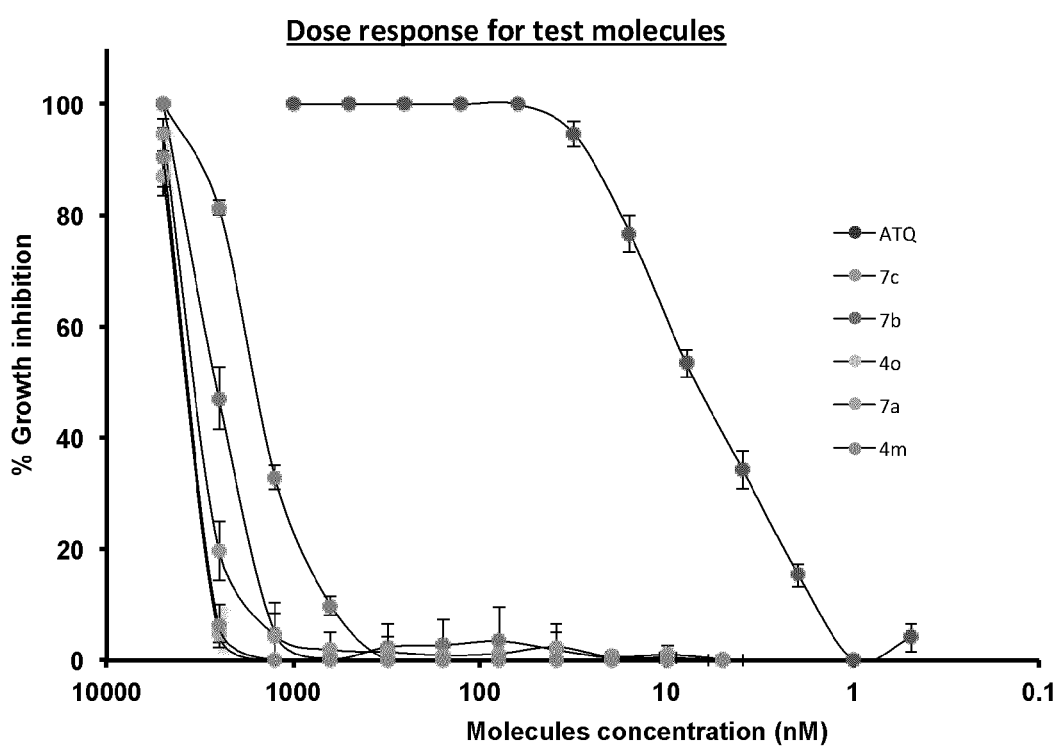
FIG. 2: *P. falciparum* dose response curve for test molecules using serial 10-fold dilutions of the molecules. Standard anti-malarial ATQ is used as a comparator.

Data from the preliminary screen (at 10 µM only) is shown in FIG. 1 and data from the dose response experiment is shown in FIG. 2. The IC$_{50}$ values for the selected molecules are tabulated in Table-5.

TABLE 5

IC50 values for selected molecules used in the dose response assay.

| Compound | IC$_{50}$ value (nM) |
|---|---|
| 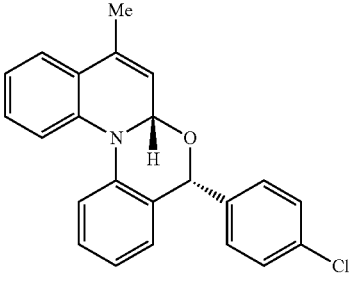 4m | 3800 |
| 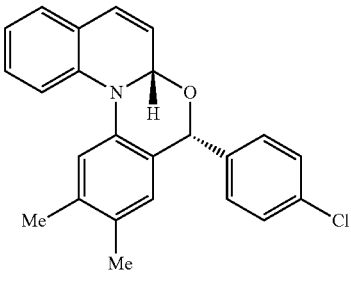 4o | 3511 |
| 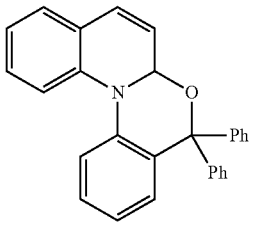 7a | 3874 |
| 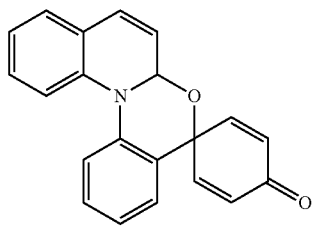 7b | 1692 |
| 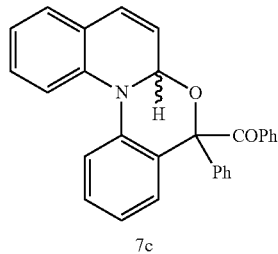 7c | 2639 |
| Atovaquone | 7.11 |

Example 33

Formulation Experiments

Composition

Compound 4a: 10.0% w/w (10.0 mg)
Strawberry Flavor: 0.7% w/w (0.7 mg)
Color Iron oxide red: 0.3% w/w (0.3 mg)
Magnesium stearate: 2.0% w/w (2.0 mg)
Mannitol: q.s. to 100.0% w/w (87.0 mg)

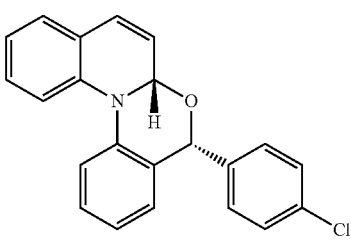

4a

Procedure:

Mannitol was dissolved in 2.0 ml water followed by addition of iron oxide red and strawberry flavor, then the mixture was dried using rotary evaporator followed by addition of 4a and magnesium stearate and mixed properly with pestle and filled in a sample vial.

Example 34

Composition

Compound 7c: 10.0% w/w (10.0 mg)
Strawberry Flavor: 0.7% w/w (0.7 mg)
Color Iron oxide red: 0.3% w/w (0.3 mg)
Magnesium stearate: 2.0% w/w (2.0 mg)
Mannitol: q.s. to 100.0% w/w (87.0 mg)

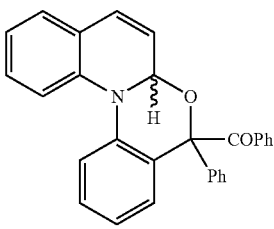

7c

Procedure:

Mannitol was dissolved in 2.0 ml water followed by addition of iron oxide red and strawberry flavor, then the mixture was dried using rotary evaporator followed by addition of 7c and magnesium stearate and mixed properly with pestle and filled in a sample vial.

Example 35

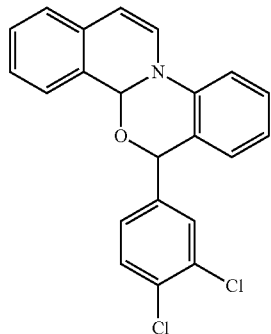

Composition
Compound 9g: 10.0% w/w (10.0 mg)
Strawberry Flavor: 0.7% w/w (0.7 mg)
Color Iron oxide red: 0.3% w/w (0.3 mg)
Magnesium stearate: 2.0% w/w (2.0 mg)
Mannitol: q.s. to 100.0% w/w (87.0 mg)
Procedure:

Mannitol was dissolved in 2.0 ml water followed by addition of iron oxide red and strawberry flavor, then the mixture was dried using rotary evaporator followed by addition of 9g and magnesium stearate and mixed properly with pestle and filled in a sample vial.

Advantages of the Embodiments:
1) Transition—Metal free approach
2) High yield and selectivity of the products by the instant process
3) Easily available cheap staring material
4) Industrially and economically feasible process
5) Compounds possess anti-malarial activity All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:
1. A benzoxazino quinoline derivative compound of Formula (I):

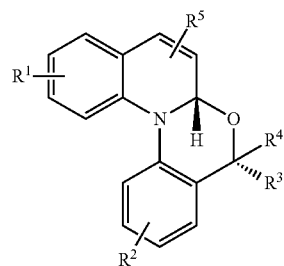

Formula (I)

wherein
$R^1$ is selected from the group consisting of H and ($C_2$ to $C_6$) alkoxy;
$R^2$ is selected from the group consisting of H, ($C_1$ to $C_6$) alkyl, aryl, fluoro, and dioxane ring O—($CH_2$)—O, wherein the aryl is unsubstituted or substituted with one or more substituents selected from the group consisting of halogens and methoxy;
$R^3$ is selected from the group consisting of H, arylalkyl, cycloalkyl, ferrocene, —COR, 4-methoxyphenyl, 3,4-dichlorophenyl, naphthalen-2-yl, thiophen-2-yl, thiophen-3-yl, aryl substituted with methoxy, and aryl substituted with more than one halogen;
$R^4$ is selected from the group consisting of H, arylalkyl, cyclohexyl, ferrocene, —COR, 4-methoxyphenyl, 3,4-dichlorophenyl, naphthalen-2-yl, thiophen-2-yl, thiophen-3-yl, aryl substituted with methoxy, and aryl substituted with more than one halogen;
R is selected from the group consisting of aryl and alkoxy, wherein the aryl is unsubstituted or substituted with one or more substituents selected from the group consisting of halogens and methoxy;
$R^5$ is selected from the group consisting of hydrogen and ($C_1$ to $C_6$) alkyl,
wherein $R^3$ and $R^4$ are independent groups or $R^3$ and $R^4$ together with the atom to which they are attached form a six membered-dien-4-one ring.

2. The compound of claim 1, selected from the group consisting of:
5-(4-methoxyphenyl)-5H,6aH-benzo[4,5][1,3]oxazino[3,2-a]quinoline,
5-(2-fluorophenyl)-5H,6aH-benzo[4,5][1,3]oxazino[3,2-a]quinoline,
5-(3,4-dichlorophenyl)-5H,6aH-benzo[4,5][1,3]oxazino[3,2-a]quinoline,
5-(naphthalen-2-yl)-5H,6aH-benzo[4,5][1,3]oxazino[3,2-a]quinoline,
5-(thiophen-2-yl)-5H,6aH-benzo[4,5][1,3]oxazino[3,2-a]quinoline,
5-(thiophen-3-yl)-5H,6aH-benzo[4,5][1,3]oxazino[3,2-a]quinoline,
5-ferrocineyl-5H,6aH-benzo[4,5][1,3]oxazino[3,2-a]quinoline,
5-cyclohexyl-5H,6aH-benzo[4,5][1,3]oxazino[3,2-a]quinoline,
5-(4-chlorophenyl)-8-methyl-5H,6aH-benzo[4,5][1,3]oxazino[3,2-a]quinoline,
5-(4-chlorophenyl)-12-methoxy-5H,6aH-benzo[4,5][1,3]oxazino[3,2-a]quinoline,
5-(4-chlorophenyl)-2,3-dimethyl-5H,6aH-benzo[4,5][1,3]oxazino[3,2-a]quinoline,
5-(4-chlorophenyl)-2,3-difluoro-5H,6aH-benzo[4,5][1,3]oxazino[3,2-a]quinoline, 8-(4-chlorophenyl)-6aH,8H-[1,3]dioxolo[4",5":4',5']
benzo[1',2':4,5][1,3]oxazino[3,2-a]quinoline,
6aH-spiro[benzo[4,5][1,3]oxazino[3,2-a]quinoline-5,1'-cyclohexane]-2',5'-dien-4'-one,
phenyl(5-phenyl-5H,6aH-benzo[4,5][1,3]oxazino[3,2-a]quinolin-5-yl)methanone, and
thiophen-2-yl(5-(thiophen-2-yl)-5H,6aH-benzo[4,5][1,3]oxazino[3,2-a]quinolin-5-yl)methanone.

3. A process for the preparation of a benzoxazino quinoline derivative compound of Formula (I):

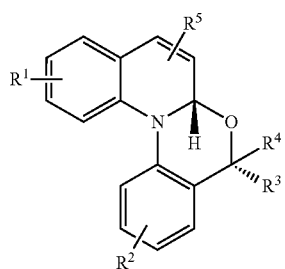

Formula (I)

wherein
R¹ is selected from the group consisting of H and ($C_2$ to $C_6$) alkoxy;
R² is selected from the group consisting of H, ($C_1$ to $C_6$) allyl, aryl, fluoro, and dioxane ring O—($CH_2$)—O, wherein the aryl is unsubstituted or substituted with one or more substituents selected from the group consisting of halogens and methoxy;
R³ is selected from the group consisting of H, arylalkyl, cycloalkyl, ferrocene, —COR, 4-methoxyphenyl, 3,4-dichlorophenyl, naphthalen-2-yl, thiophen-2-yl, thiophen-3-yl, aryl substituted with methoxy, and aryl substituted with more than one halogen;
R⁴ is selected from the group consisting of H, arylalkyl, cyclohexyl, ferrocene, —COR, 4-methoxyphenyl, 3,4-dichlorophenyl, naphthalen-2-yl, thiophen-2-yl, thiophen-3-yl, aryl substituted with methoxy, and aryl substituted with more than one halogen;
R is selected from the group consisting of aryl and alkoxy, wherein the aryl is unsubstituted or substituted with one or more substituents selected from the group consisting of halogens and methoxy;
R⁵ is selected from the group consisting of hydrogen and ($C_1$ to $C_6$) alkyl,
wherein R³ and R⁴ are independent groups or R³ and R⁴ together with the atom to which they are attached form a six membered-dien-4-one ring, comprising:
a) dissolving a mixture of 18-crown-6, KF and a carbonyl compound in THF under argon atmosphere followed by stirring for 5 min at –10° C. to obtain a reaction mixture a);
b) adding quinoline and a trifluoromethanesulfonate to the reaction mixture a) followed by stirring for 12 hrs at room temperature to obtain a reaction mixture b); and
c) purifying the reaction mixture b) by column chromatography to obtain a benzoxazino quinolone derivative of Formula (I).

4. The process of claim 3, wherein the carbonyl compound is selected from the group consisting of 4-chlorobenzaldehyde, 2-fluorobenzaldehyde, 4-fluorobenzaldehyde, 4 bromobenzaldehyde, 3,4-dichlorobenzaldehyde, 4-methoxybenzaldehyde, 2-naphthaldehyde, 2-Thiophenecarboxaldehyde, 3-Thiophenecarboxaldehyde, ferrocenecarboxaldehyde, cyclohexanecarbaldehyde, benzophenone, benzoquinone, 1,2-di(thiophen-2-yl)ethane-1,2-dione, and 4-methyl-benzaldehyde.

5. The process of claim 3, wherein the trifluoromethanesulfonate compound is selected from the group consisting of 2-(trimethylsilyl)phenyl trifluoromethane sulfonate, 4,5-dimethyl-2-(trimethylsilyl)phenyl trifluoromethanesulfonate, 4,5-difluoro-2-(trimethylsilyl)phenyl trifluoromethanesulfonate, 6-(trimethylsilyl)benzo[d][1,3]dioxol-5-yl trifluoromethanesulfonate, 2-(trimethylsilyl)naphthalen-1-yl trifluoromethane-sulfonate, and 4,5-dimethyl-2-(trimethylsilyl)phenyl trifluoromethanesulfonate.

6. A pharmaceutical composition comprising the compound of claim 1 and one or more pharmaceutically acceptable ingredients.

7. A method of treating malaria, comprising administering the compound of claim 1 to a patient in need thereof.

8. A benzoxazino isoquinoline derivative compound having a formula selected from the group consisting of:

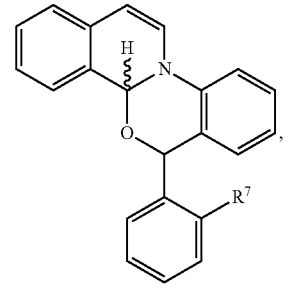

,

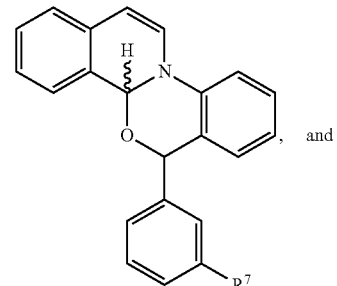

, and

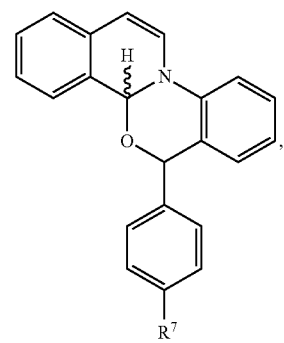

, wherein R⁷ is alkyl.

9. The compound of claim 8, consisting of:
6-(p-tolyl)-4bH,6H-benzo[4,5][1,3]oxazino[2,3-a]isoquinoline.

10. A process for the preparation of the compound of claim 8, comprising:
   a) dissolving a mixture of 18-crown-6, KF and carbonyl compound in THF under argon atmosphere followed by stirring for 5 min at −10° C. to obtain a reaction mixture a);
   b) adding isoquinoline and a trifluoromethanesulfonate compound to the reaction mixture a) followed by stirring for 12 hrs at room temperature to obtain reaction mixture b); and
   c) purifying the reaction mixture b) by column chromatography to obtain the benzoxazino isoquinolone derivative compound.

11. The process of claim 10, wherein the carbonyl compound is 4 methyl-benzaldehyde.

12. A process for the preparation of a benzoxazino isoquinoline derivative compound having a formula selected from the group consisting of:

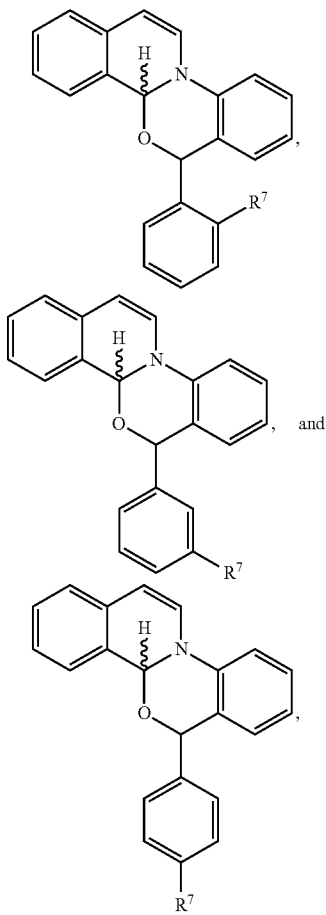

wherein $R^7$ is alkyl, comprising:

a) dissolving a mixture of 18-crown-6, KF and carbonyl compound in THF under argon atmosphere followed by stirring for 5 min at −10° C. to obtain a reaction mixture a);
   b) adding isoquinoline and 2-(trimethylsilyl)phenyl trifluoromethane sulfonate to the reaction mixture a) followed by stirring for 12 hrs at room temperature to obtain reaction mixture b); and
   c) purifying the reaction mixture b) by column chromatography to obtain the benzoxazino isoquinolone derivative compound of Formula (II).

13. A pharmaceutical composition comprising the compound of claim 8 and one or more pharmaceutically acceptable ingredients.

14. A method of treating malaria, comprising administering to a patient in need thereof a benzoxazino isoquinoline derivative compound having a formula selected from the group consisting of:

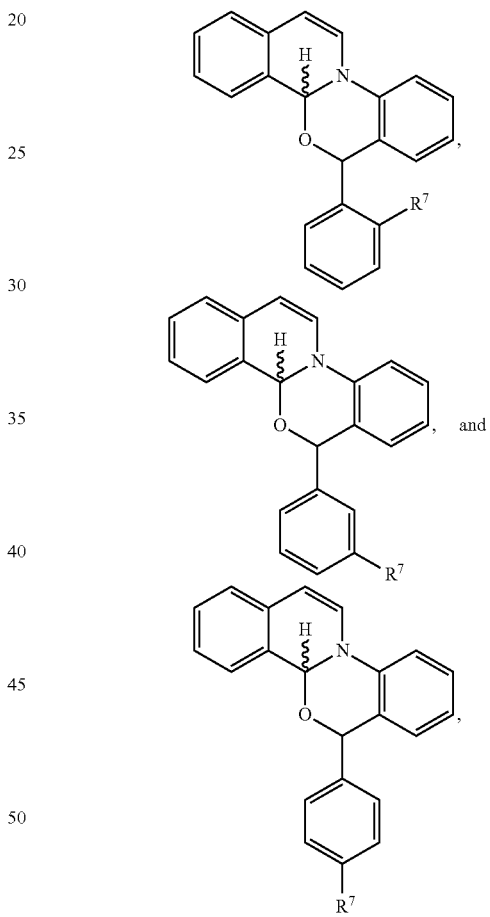

wherein $R^7$ is alkyl.

* * * * *